(12) United States Patent
Vogt et al.

(10) Patent No.: US 11,510,791 B2
(45) Date of Patent: Nov. 29, 2022

(54) MEDICAL IMPLANT FOR GAS EXCHANGE

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 105 days.

(21) Appl. No.: 16/880,366

(22) Filed: May 21, 2020

(65) Prior Publication Data

US 2020/0390567 A1   Dec. 17, 2020

(30) Foreign Application Priority Data

Jun. 12, 2019 (DE) .......................... 102019115933.4

(51) Int. Cl.
    *A61F 2/46* (2006.01)
    *A61F 2/28* (2006.01)
    *A61F 2/30* (2006.01)

(52) U.S. Cl.
    CPC .............. *A61F 2/4675* (2013.01); *A61F 2/28* (2013.01); *A61F 2/30767* (2013.01);
    (Continued)

(58) Field of Classification Search
    CPC ...... A61F 2/4675; A61F 2/28; A61F 2/30767; A61F 2002/30062; A61F 2002/30677;
    (Continued)

(56) References Cited

U.S. PATENT DOCUMENTS

| 4,631,053 A | 12/1986 | Taheri |
| 4,671,287 A | 6/1987 | Fiddian-Green |

(Continued)

FOREIGN PATENT DOCUMENTS

| JP | 2004147926 | 5/2004 |
| WO | 2007/106591 | 9/2007 |

OTHER PUBLICATIONS

Dreesmann, H, Aus Der Bonner Chirurgischen Klinik Des Prof. Dr. Trendelenburg XXIII "Ueber Knochenplombierung" ("About Bone Filling") Klinische Chirurgie pp. 804-810 and 13 pages of drawings (20 pages total) (1892) (with Computer Generated English translation attached).

(Continued)

*Primary Examiner* — Brian A Dukert
(74) *Attorney, Agent, or Firm* — Dicke, Billig & Czaja, PLLC

(57) ABSTRACT

A medical implant for treating bone defects. The implant has at least one hollow body delimiting an inner chamber in the interior of the hollow body, a fluid feed line connected in a fluid-permeable manner with the inner chamber, and a fluid discharge line connected in a fluid-permeable manner with the inner chamber. The hollow body consists at least in places or wholly of at least one plastic material that is impermeable to liquids and permeable to oxygen and to carbon dioxide, such that oxygen is deliverable from a fluid passed through the hollow body to, and carbon dioxide is absorbable into the fluid from, the surroundings of the hollow body. Also disclosed is a bone defect treatment system having such a medical implant and the fluid, wherein the fluid contains oxygen and is suitable for absorbing oxygen, and to a method for gas-flushing a surface of a medical implant.

26 Claims, 13 Drawing Sheets

(52) U.S. Cl.
CPC ............... *A61F 2002/30062* (2013.01); *A61F 2002/30677* (2013.01); *A61F 2310/00359* (2013.01)

(58) Field of Classification Search
CPC .. A61F 2002/4676; A61F 2310/00359; A61M 2202/0208; A61M 2202/0476; A61M 2202/0225; A61M 3/02; A61M 3/0204; A61M 3/0233; A61M 3/0283; A61M 1/0058; A61M 1/77; A61M 5/14276; A61M 60/122; A61M 60/855

See application file for complete search history.

(56) References Cited

U.S. PATENT DOCUMENTS

| | | | |
|---|---|---|---|
| 5,098,376 | A | 3/1992 | Berry et al. |
| 5,219,326 | A | 6/1993 | Hattler |
| 5,776,047 | A | 7/1998 | Fukunaga et al. |
| 6,443,988 | B2 | 9/2002 | Felt et al. |
| 8,435,213 | B2* | 5/2013 | Cornet ................ A61M 1/90 604/289 |
| 2001/0004710 | A1 | 6/2001 | Felt et al. |
| 2005/0119745 | A1 | 6/2005 | Tabata et al. |
| 2005/0137579 | A1* | 6/2005 | Heruth .............. A61M 5/14276 604/536 |
| 2006/0264810 | A1 | 11/2006 | Hattler et al. |
| 2010/0185299 | A1* | 7/2010 | Nies ..................... A61F 2/28 623/23.6 |
| 2010/0196439 | A1* | 8/2010 | Beck .................... A61L 27/3616 424/424 |
| 2016/0235902 | A1 | 8/2016 | Flanagan et al. |
| 2018/0368981 | A1* | 12/2018 | Mattes ................... A61L 27/50 |

OTHER PUBLICATIONS

Office Action from corresponding Canadian Patent Application 3081241 dated Jul. 8, 2021.
Office Action from corresponding Japanese Patent Application 2020-099464 dated Jul. 27, 2021.
Vallet-Regí, María and González-Calbet, José María "Calcium phosphates as substitution of bone tissues" Progress in Solid State Chemistry 32 (1-2) pp. 1-31 (2004).
Bucholz, Robert W. et al. "Hydroxyapatite and Tricalcium Phosphate Bone Graft Substitutes" The Orthopedic Clinics of North America—Bone Graft—vol. 18, No. 2 (W.B. Saunders Company) pp. 323-334 (1987).
Oonishi, Hironubu et al. "Particulate Bioglass Compared With Hydroxyapatite as a Bone Graft Substitute" Clinical Drthopaedics and Related Research 334, pp. 316-325 (Jan. 1997).
Bolander, Mark E. and Balian, Gary, "The Use of Demineralized Bone Matrix in the Repair of Segmental Defects Augmentation With Extracted Matrix Proteins And Comparison With Autologous Grafts." The Journal of Bone and Joint Surgery vol. 68(A) pp. 1264-1274 (Oct. 1986).
Higashi, Shoichiro et al. "Polymer-hydroxyapatite composites for biodegradable bone fillers" Biomaterials vol. 7 pp. 183-187 (May 1986).
Matsunaga, Katsuji et al., "Gas Permeability of Thermoplastic Polyurethane Elastomers" Polymer Journal, vol. 37, No. 6, pp. 413-417 (2005).

* cited by examiner

MEDICAL IMPLANT FOR GAS EXCHANGE

CROSS-REFERENCE TO RELATED APPLICATIONS

This application claims priority under 35 U.S.C. § 119(a) to German (DE) Patent Application No. 10 2019 115 933.4, filed on Jun. 12, 2019.

TECHNICAL FIELD

The invention relates to a medical implant for treating bone defects and to a bone defect treatment system having such an implant. The invention also relates to a method for gas-flushing a surface of a medical implant. The subject matter of the invention is thus a medical implant for temporary implantation in bone cavities.

BACKGROUND OF THE DISCLOSURE

Bone defects in humans may have many and varied causes, frequent causes being trauma and infections. Bone defects do not heal spontaneously if they exceed a critical size, such defects then being known as "critical-size defects." To treat bone defects, bone substitute materials of the most varied structure and composition are used in clinical practice, as well as allogeneic bone tissue and autologous bone tissue.

Bone substitute materials have been known for decades and can be made from the most varied materials. Typical inorganic bone substitute materials are calcium sulfate (H. Dreesmann: Über Knochenplombierung. ("Bone Filling"), Klinische Chirurgie (1892) 804-810), carbonate apatite (M. V. Vallet-Regi, J. M. Gonzalez-Cabbet: Calciumphosphates as substitution of bone tissues. Progress in Solid State Chemistry 32 (1-2) (2004)1-31), hydroxyapatite, β-tricalcium phosphate (R. W. Bucholz, A. Carlton, R. E. Holmes: hydroxy-apatite and tricalciumphosphate bone graft substitutes. The Orthopedic Clinics of North America 18(2) (1987) 323-334), bioglasses (H. Oonishi et al.: Particulate bioglass compared with hydroxyapatite as bone graft substitute. Clinical Orthopaedics and Related Research 334(1997) 316-325) and demineralized bone matrix (M. E. Bolander, G. Balian: The use of demineralized bone matrix in the repair of segmental defects. Augmentation with extracted matrix proteins and comparison with autologous grafts. The Journal of bone and Joint Surgery American Volume 68(8) 1986) 1264-1274). In addition, organic-based bone substitute substances, such as for example polyester, and also combinations of inorganic and organic materials have also been used to produce bone substitute materials (S. Higashi et al.: Polymerhydroxyapatite composites for biodegradable bone fillers. Biomaterials 7(3) (1986) 183-187).

In the field of dentistry bone substitute materials have been successfully used for relatively small bone defects. With larger bone defects in the limb regions it is very commonly observed clinically that the bone tissue grows only superficially into the bone substitute material even when porous bone substitute materials are used. Similar problems arise in the transplantation of autologous bone tissue and also in the case of combinations of autologous bone material and inorganic bone substitute materials. The autologous tissue which is situated furthest from the bone tissue with good blood supply is frequently damaged and very often dies off.

The problem addressed by the present invention may thus be considered that of finding a way of improving healing chances, and optionally of providing a medical implant for that purpose. Stabilization and ossification of the bone defect should be achieved as quickly as possible and in as uncomplicated a manner as possible. Further measures may also be used to influence the healing process positively.

It has been found, in the context of the present invention, that a significant reason for the observation that autologous tissue situated furthest from bone tissue with a good blood supply is frequently damaged and very often dies off is very probably that these regions can no longer be sufficiently supplied with oxygen and that removal of the carbon dioxide arising during metabolism and of further metabolic products is possible only with difficulty, because no blood vessels are present in the interior of the bone substitute material with which the flowing blood ensures transport of oxygen and removal of the carbon dioxide formed.

An object of the invention thus consists in the development of a temporary medical implant, which is intended to allow gas exchange with its surroundings. The implant is intended to be in a position to deliver oxygen at its surface to the surroundings and to absorb and remove carbon dioxide from the surroundings. The oxygen delivery and the absorption are intended to be possible continuously or indeed discontinuously. Gas exchange and gas transport are intended to be achieved by a fluid intended to flow through the medical implant. The medical implant is intended to be removable and should not be able to grow together with human or animal tissue. The temporary medical implant is intended to enable gas exchange with surrounding bone substitute materials and in particular with autologous bone tissue and also with bone substitute materials colonized with cells, such as osteoblasts. In this way, it is intended to keep the cells alive, in particular the osteoblasts, after implantation in a relatively large bone defect until the cells can be supplied with oxygen by newly formed blood vessels. As soon as these have been formed by the organism, it is intended to be able to remove the temporary implant.

A further object of the invention is the development of a bone substitute material system containing as a constituent part the temporary medical implant to be developed.

An additional object of the present invention is to develop a non-medical method with which oxygen can be delivered into a cavity and at the same time carbon dioxide can be absorbed from the cavity. The method is intended to be performable with the medical implant according to the invention and applied in cavities which are not part of a human or animal body.

In addition to its place-holding function, the medical implant is also intended for gas exchange with the surrounding tissue, wherein oxygen or an oxygen-containing flushing gas mixture or an oxygen-enriched flushing liquid flows as fluid through the inner chamber of the spacer continuously or discontinuously and oxygen may be fed via the permeable outer wall of the implant to the tissue and carbon dioxide simultaneously taken away therefrom.

SUMMARY OF THE DISCLOSURE

The objects of the invention are achieved by a medical implant for treating bone defects having at least one hollow body, with an inner chamber in the interior of the hollow body, a fluid feed line, which is connected in a fluid-permeable manner with the inner chamber of the hollow body, and a fluid discharge line, which is connected in a fluid-permeable manner with the inner chamber of the hollow body, wherein the hollow body consists at least in places or wholly of at least one plastic material, wherein the at least one plastic material is impermeable to liquids and is permeable to oxygen and to carbon dioxide, such that oxygen is deliverable from a fluid passed through the hollow body to the surroundings of the hollow body and carbon dioxide is absorbable from the surroundings of the hollow body into the fluid.

The medical implant is preferably a temporary medical implant.

The fluid passed through the hollow body must be suitable to deliver oxygen and to absorb carbon dioxide.

Preferably, the medical implant is suitable for temporary implantation in bone cavities.

Further preferably, the hollow body is made from an oxygen- and carbon dioxide-permeable plastic material.

Still further, the inner chamber is closed off relative to the surroundings of the medical implant.

The at least one plastic material preferably at least in places forms a continuous wall of the hollow body. That is to say, there are regions of the wall of the hollow body which consist of no other additional material apart from the at least one plastic material. Readily permeable meshes and wires, in particular of metal, are unproblematic in this respect. The intention is hereby to ensure that the permeability of the plastic material to oxygen and carbon dioxide can be used to ensure that the wall of the hollow body is likewise permeable to oxygen and carbon dioxide at least in these regions.

Preferably, a wall delimiting the inner chamber of the hollow body is permeable to oxygen and carbon dioxide.

According to a preferred embodiment of the present invention, the hollow body has a tubular configuration, wherein the fluid feed line and the fluid discharge line are preferably connected at one end face of the hollow body or are connected at two mutually opposing end faces of the hollow body with the inner chamber of the hollow body. Tubular hollow bodies are particularly well suited to use as spacers in particular for bone defects of the long tubular bones.

The hollow body may also have any other desired shape, depending on the size and shape of the bone defect to be temporarily filled.

The fluid may be gaseous or liquid. Mixtures of liquids and gases are also possible. Preferred fluids are air, oxygen, oxygen-saturated saline, oxygen-saturated Ringer's solution, oxygen-saturated Ringer's lactate solution, oxygen-saturated phosphate buffer solution and oxygen-saturated perfluorodecalin and mixtures thereof. It is essential that the fluid contains oxygen and that the fluid can absorb carbon dioxide. All fluids are therefore suitable which can transport oxygen and carbon dioxide and can exchange these substances with the surroundings via the permeable wall of the hollow body.

According to the invention, the hollow body or the at least one plastic material of the hollow body has a permeability coefficient for oxygen of greater than or equal to 0.5 $cm^3/(m^2 \cdot d \cdot bar)$ and a permeability coefficient for carbon dioxide of greater than or equal to 0.5 $cm^3/(m^2 \cdot d \cdot bar)$, preferably to have a permeability coefficient for oxygen of greater than or equal to 1 $cm^3/(m^2 \cdot d \cdot bar)$ and a permeability coefficient for carbon dioxide of greater than or equal to 1 $cm^3/(m^2 \cdot d \cdot bar)$. The unit d denotes a day.

In this way, the surroundings of the medical implant may be well supplied with oxygen and carbon dioxide may be readily transported away from the surroundings of the medical implant and in the process out from the inside of the treatment site.

The permeability coefficient is determined pursuant to DIN 53380-4 (11/2006). This relates in particular to testing plastic material, here to the determination of gas permeability, wherein Part 4 of DIN 53380 standardizes a carbon dioxide-specific infrared absorption method for measurement of plastic films and plastic moldings which may also be applied to oxygen. Such measurements are performed and offered for sale for example by Mecadi GmbH (Bexbach, Germany).

The hollow body or the at least one plastic material of the hollow body has a permeability coefficient for oxygen of greater than or equal to 0.5 $cm^3/(m^2 \cdot d \cdot bar)$ and a permeability coefficient for carbon dioxide of greater than or equal to 0.5 $cm^3/(m^2 \cdot d \cdot bar)$ pursuant to DIN 53380-4 (11/2006), preferably to have a permeability coefficient for oxygen of greater than or equal to 1 $cm^3/(m^2 \cdot d \cdot bar)$ and a permeability coefficient for carbon dioxide of greater than or equal to 1 $cm^3/(m^2 \cdot d \cdot bar)$ pursuant to DIN 53380-4 (11/2006).

In solids, permeability generally denotes the property of allowing gases and/or liquids to pass. In the present case, this relates to the permeability of the walls of the hollow body specifically in relation to molecular oxygen and molecular carbon dioxide in gaseous form. The permeability coefficient is a material-specific constant and is a measure of permeability for liquids and gases.

The fluid feed line and the fluid discharge line lead in such a way into the hollow body that, when the fluid from the fluid feed line flows through the hollow body into the fluid discharge line, the fluid flows over an entire inner surface of the hollow body or at least over 50% of the entire inner surface of the hollow body.

In this way, on flow through the hollow body a sufficiently long period of contact between the through-flowing fluid and the internal wall of the hollow body or of the at least one plastic material is achieved, so promoting gas exchange of oxygen and carbon dioxide through the wall of the hollow body or of the at least one plastic material.

If the hollow body is constructed with a main part and with a plurality of branches extending away from the main part, the branches also count as part of the flowed-over surface, even if the majority of the fluid flow is along the main part past the branches. What is critical here is that the inner surfaces of the branches are accessible starting from the main fluid stream.

An inflow opening of the gas infeed hose, with which the fluid feed line leads into the inner chamber, is arranged spatially separately from an outflow opening of the fluid discharge line, wherein the outflow opening forms the point where the inner chamber opens into the gas discharge hose.

This ensures gas exchange over the entire wall of the hollow body or over large regions of the wall of the hollow body. The inflow opening is the opening of the fluid feed line through which the fluid flows from the fluid feed line into the inner chamber of the hollow body. The outflow opening is accordingly the opening of the fluid discharge line through which the fluid flows out into the fluid discharge line from the inner chamber of the hollow body.

Provision may in this respect be made for the inflow opening of the fluid feed line to be arranged at a first end of the hollow body and for the outflow opening to be arranged at a second end of the hollow body opposite the first end.

The residence time of the through-flowing fluid against the internal wall of the hollow body or against the internal wall of the at least one plastic material is thereby increased and gas exchange through the hollow body or the at least one plastic material improved.

In certain embodiments, the fluid feed line and the fluid discharge line both are jointly connected with the hollow body on one side of the hollow body.

This simplifies insertion of the implant into the cavity in the patient's bone. In addition, in the ideal case the only accesses to the hollow body and the treatment site are located close together, so reducing the risk of microbial contamination.

According to a further embodiment of the present invention, a sterile filter is arranged in the fluid feed line and/or the fluid discharge line which is impermeable to microbes but permeable to gases.

This reduces the risk of infection for the treated patient and the attending personnel.

According to one preferred embodiment of the present invention, a valve, in particular a one-way valve, is arranged in the fluid feed line and/or the fluid discharge line, wherein the one-way valve is preferably a non-return valve.

Use of a one-way valve or a non-return valve reliably precludes backflow of the fluid. In addition, a suitably adjustable valve can be used to adjust the pressure in the interior of the hollow body and so achieve a specific shape or a specific rigidity of the medical implant.

According to a preferred further development, the valve is arranged in the fluid discharge line and configured as a pressure relief valve, wherein the opening pressure of the pressure relief valve is preferably adjustable.

The expanded state of the hollow body may thereby be reliably achieved and also maintained.

A one-way valve in the fluid discharge line may ensure that a pressure may be built up with the fluid in the interior of the hollow body and that the fluid used cannot pass back into the hollow body. Preferably, a one-way valve is arranged in the fluid discharge line.

The fluid feed line and the fluid discharge line consist of a material which is impermeable to oxygen and carbon dioxide, preferably a plastic material impermeable to oxygen and carbon dioxide.

In this way, the oxygen is prevented from exiting prematurely from the fluid. In addition, the fluid feed line and the fluid discharge line may in this way be made of an inexpensive plastic material.

The hollow body or the at least one plastic material of the hollow body contain at least one antiseptic active ingredient or are coated with at least one antiseptic active ingredient.

In this way, the surface of the medical implant and the surroundings of the medical implant in the patient's body may be disinfected with the at least one antiseptic active ingredient. In this way, treatment complications are avoided.

The hollow body is a hollow cylinder or the hollow body has a main part in the form of a hollow cylinder, wherein the fluid feed line and the fluid discharge line lead into the hollow cylinder in the region of opposing base faces of the hollow cylinder, wherein the hollow cylinder preferably coaxially surrounds a part of the fluid feed line or of the fluid discharge line.

As a result of the cylindrical shape, the implant may be introduced into bone defects in tubular bones. It may additionally be ensured that the fluid flows over as large as possible a surface of the wall of the hollow body, so assisting gas exchange.

Preferably, the hollow body is embodied as a perforated metal body or plastic material body, the outside of which is covered with a plastic layer permeable to oxygen and to carbon dioxide.

This makes it possible to produce a mechanically loadable medical implant and at the same time to ensure gas exchange through the wall of the hollow body.

To improve the workability of the hollow body, the hollow body has a plastically deformable plastic jacket permeable to oxygen and carbon dioxide, wherein the plastic jacket preferably contains spiral metal wires and/or metal wires arranged in a reticular manner.

The medical implant may thereby be shaped according to anatomical conditions and optionally retains the selected shape due to the rigidity of the metal wires.

So as to open up additional treatment options, a line with a plurality of openings is arranged on the hollow body for delivering an active ingredient, wherein the line is connected with an active ingredient feed line, wherein the sum of the free cross-sectional areas of the openings is preferably less than the free cross-section of the line and of the active ingredient feed line.

With this development it is possible to apply pharmaceutical active ingredient solutions locally. Pharmaceutical active ingredients considered in this context are antibiotics, antiseptics, anti-inflammatory agents, bisphosphonates, growth factors, bacteriophages, lysostaphin and muramidases. It is also possible to introduce cell suspensions through the active ingredient feed line into the surroundings of the implant and enable colonization of the structures surrounding the medical implant.

The line with the openings also makes it possible to force antiseptic or antibiotic solutions through the openings to the surroundings of the medical implant. Antimicrobial protection of the surface of the medical implant is also made possible by the line. It is also possible to introduce liquid or gel-type antibiotic or antiseptic pharmaceutical preparations through the line which may migrate through diffusion into the surroundings and so be used to treat the patient in the region of the medical implant.

The at least one plastic material is an elastic and/or plastic, non-biodegradable plastic material, wherein the at least one plastic material is preferably selected from polyurethane, ethylene-propylene-diene rubber EPDM and silicone, or the at least one plastic material is an elastic and/or plastic biodegradable plastic material, wherein the at least one plastic material is preferably selected from gelatin, crosslinked collagen and crosslinked albumin.

These two options make it possible to provide a readily removable medical implant (non-biodegradable plastic material) or for the medical implant to be partly or completely broken down in the body (biodegradable plastic material) and not to have to be removed again or not completely.

The hollow body is expandable and/or contractable by changing the pressure in the inner chamber thereof relative to the surrounding atmosphere.

When using a dimensionally non-stable, elastic implant material, the selected shape of the hollow body may be ensured by a suitable internal pressure of the hollow body. Insertion and removal of the medical implant may additionally be simplified in this way.

According to a preferred variant of the present invention, the hollow body has a main part and a plurality of branches extending laterally therefrom, wherein the inner chamber of the hollow body extends in the main part and in the branches and the fluid feed line and the fluid discharge line are connected with the main part, wherein preferably at least the branches or walls of the branches consist of the plastic material or are constructed using the plastic material.

The inner chamber preferably has a smaller cross-section in the branches than in the main part.

In this way, the surface of the hollow body may be enlarged and thus a greater quantity of cells supplied, in particular supplied extracorporeally.

The hollow body consists of at least one absorbable and/or biodegradable material.

In this way, the hollow body may remain in the body and be broken down therein without it having to be removed from the body again. The fluid feed line and the fluid discharge line may to this end be simply separated.

These variants enable the extracorporeal multiplication of cells in cavities of cell culture vessels. Possible growth-promoting substances are, for example, tricalcium phosphate or substances with a similar action. The cells multiplied in this way may then be implanted together with the medical implant or indeed without the medical implant. If the hollow body is constructed from a crosslinked gelatin or biopolymer, the medical implant may be broken down apart from the connectors. The same is also possible if the hollow body is made from degradable hollow fibers.

The hollow body or the entire medical implant has a three-dimensional structure that is foldable. In this way, the medical implant may be adaptable to the shape of the cavity to be treated.

The medical implant may be used as an aeratable scaffold for cell culturing. In tissue engineering, a "scaffold" is an umbrella term for the artificial production of biological tissue using directed culturing of cells to replace or regenerate diseased tissue in a patient. No medical treatment of a patient is needed for this, as this takes place only later on with the assistance of the artificially produced cells. The medical implant may then be used as a supporting structure for cell cultures.

The objects underlying the present invention are also achieved by a bone defect treatment system having such a medical implant according to the invention and the fluid, wherein the fluid contains oxygen and is suitable for absorbing carbon dioxide.

In this way, a complete system (bone defect treatment system) is provided, in which the fluid may already be matched to the medical implant or both may be matched to the treatment site.

In this case, the fluid is selected from air, oxygen, oxygen-saturated saline, oxygen-saturated Ringer's solution, oxygen-saturated Ringer's lactate solution, oxygen-saturated phosphate buffer solution and oxygen-saturated perfluorodecalin or a mixture of at least two of the stated gases or liquids.

These fluids are well suited to delivering oxygen and absorbing carbon dioxide. In addition, many of these fluids are safe as regards health.

In this case furthermore the bone defect treatment system includes a bone substitute material, wherein preferably the bone substitute material is applied to the external surface of the hollow body or may be applied to the external surface of the hollow body.

In this way, a more complete bone defect treatment system is provided, which contains all the constituents necessary and helpful for treatment of a bone defect.

In turn, the bone substitute material is selected from a non-biodegradable, a partially degradable or a fully biodegradable bone substitute material and mixtures thereof.

These mixtures are particularly suitable for use with the medical implant according to the invention.

Moreover, the bone substitute material is selected from autologous bone tissue, allogeneic bone tissue, hydroxyapatite, carbonate apatite, β-tricalcium phosphate, α-tricalcium phosphate, calcium dihydrate, brushite, monetite and mixtures thereof, or the bone substitute material contains living cells and/or is colonized with living cells on the surface thereof.

These bone substitute materials may be particularly readily used with the medical implant according to the invention. Supplying these bone substitute materials with oxygen and deacidification through carbon dioxide absorption have a particularly good effect for the treatment site in the case of these bone substitute materials.

It is particularly advantageous for the medical implant to be combined with autologous bone tissue and particularly preferably with autologous cancellous bone. By introducing oxygen via the hollow body, the cells of the autologous bone tissue are supplied with oxygen and at the same time the carbon dioxide released during cell metabolism is carried away. Oxygen deficiency may impede cellular respiration, such that the cells initially begin to ferment and then to die off. Fermentation processes may bring about local over-acidification. Furthermore, local over-acidification is prevented by removal of the carbon dioxide formed.

The objects underlying the present invention and relating to a non-medical method are achieved by a method for gas-flushing a surface of a medical implant, in particular a medical implant according to the invention, preferably with a bone defect treatment system according to the invention, characterized by the following steps:

A) feeding a fluid containing oxygen into an inner chamber of a hollow body of the medical implant;

B) delivering oxygen from the fluid through a plastic material delimiting the inner chamber of the hollow body to the surroundings of the hollow body;

C) absorbing carbon dioxide from the surroundings of the hollow body through the plastic material delimiting the inner chamber into the fluid; and D) passing the fluid through the inner chamber of the hollow body and discharging the fluid from the inner chamber of the hollow body.

Steps B) and C) preferably run simultaneously. In addition, the gas exchange in steps B) and C) preferably also takes place as early as during step A) and throughout step D).

Air or oxygen may be used as the fluid. It also falls within the purposes of the invention if, instead of air or oxygen as the fluid, oxygen-saturated flushing liquids, such as for example physiological saline, Ringer's solution or Ringer's lactate solution, are introduced into the expandable medical implant, in particular by the fluid feed line. It is furthermore also possible to use perfluorinated decalin as the oxygen carrier or other perfluorinated liquids in which oxygen is soluble as the fluid. These fluids may be passed back out of the hollow body by the fluid discharge line.

The method need not be performed for medical treatment of a human or animal body.

Preferably, the method is performed outside a human or an animal body.

The method according to the invention need not be performed by a doctor or a physician.

In addition to the treatment of bone defects, medical implants according to the invention also enable extracorporeal cell multiplication. To this end, cells and nutrients may be applied to the external surface of the plastic material or of the hollow body. These are then supplied with oxygen via the fluid, while carbon dioxide is removed from the growing cell cultures.

Furthermore, the hollow body can be introduced into a cavity prior to step A) and a bone substitute material can be applied to the surface of the medical implant and/or introduced into the cavity between the medical implant and the inner walls delimiting the cavity.

The cavity is preferably not a cavity of a human or animal body.

Through introduction into the cavity the advantages of the method are brought fully into play. The gas exchange between the cavity and the inner chamber of the hollow body helps to bring about the advantages according to the invention.

Finally, pro the method can be used for the extracorporeal multiplication of cells, in particular of bone cells, wherein prior to step A) the cells are applied to the external surface of the hollow body, preferably are applied together with a nutrient solution and/or growth promoting substances to the external surface of the hollow body.

In this way, already supplied cells may be introduced together with the medical implant into the bone defect, in order to accelerate healing and improve healing success.

The medical implant may be used extracorporeally to aerate and multiply a cell culture for bone cells at the surface of the hollow body. Once provided with the grown cell culture, the medical implant may subsequently be implanted and then aerated still further inside the body, in order to promote further multiplication and growth of the cells in the bone defect.

The medical implant does not have to be removed if the hollow body is biodegradable or can be broken down by the body. The connectors or the fluid feed line and the fluid discharge line may then simply be cut off at the desired time, the hollow body and the growing cells remaining in the body and being absorbed.

Underlying the invention is the surprising recognition that the medical implant makes it possible to assist in the construction of the surrounding bone structure, in that the surroundings of the medical implant are supplied with oxygen and over-acidification of the surroundings of the medical implant by carbon dioxide or carbonic acid is avoided. For these reasons, more rapid and effective ossification can be achieved, such that successful healing may take place sooner. A particular advantage is that the inside, remote from the bloodstream, of the bone, which can normally be supplied only poorly with oxygen by the bloodstream, can be better supplied using the medical implant according to the invention as the latter directly adjoins the inside of the treatment position. By using the plastic material permeable to oxygen and carbon dioxide, oxygen can be delivered reliably and uniformly from a fluid flowing through the hollow body to the surroundings of the hollow body and at the same time carbon dioxide absorbed from the surroundings of the hollow body, in order to create a climate suitable for healing of the bone defect.

It is furthermore advantageous that, after completion of the implantation phase, the hollow body can reduce its volume through application of a reduced pressure, so enabling removal of the hollow body through a small opening Removal of the carbon dioxide prevents acidification of the cells.

Once osteoblasts have grown successfully into the bone substitute material or osteoblasts have grown on the bone substitute material, the temporary implant is removed. A prerequisite for this is that sufficient neovascularization has taken place, so as to ensure the transport of oxygen and nutrients and the removal of carbon dioxide. This means the temporary implant only takes over the supply of oxygen and the removal of carbon dioxide temporarily, until the patient's own blood vessels have been reconstructed. The cavity remaining after removal of the temporary implant is either so small in diameter that spontaneous ingrowth of the bone tissue is possible or the cavity is filled in with bone substitute material, preferably granular bone substitute material.

An example of a medical implant according to the invention may have:

a) at least one hollow body permeable to oxygen and carbon dioxide but impermeable to liquids, b) at least one fluid feed line for fluids, which is connected in a fluid-permeable manner with the at least one permeable hollow body, c) at least one fluid discharge line for fluids, which is connected in a fluid-permeable manner with the at least one permeable hollow body, d) at least one fluid, which contains oxygen and is capable of absorbing carbon dioxide, wherein the fluid is passed by the fluid feed line into the inner chamber of the at least one hollow body and thence by the fluid discharge line out of the inner chamber of the at least one hollow body, e) wherein the at least one fluid is passed through the inner chamber of the at least one hollow body in such a way that oxygen from the at least one fluid may pass or permeate through the wall of the at least one hollow body into the surroundings of the at least one hollow body and carbon dioxide from the surroundings may pass or permeate into the at least one fluid in the inner chamber of the at least one hollow body.

An example of a bone substitute material system according to the invention may be composed of such a medical implant and a non-biodegradable and/or a partially degradable and/or a fully biodegradable bone substitute material, and mixtures thereof.

It is to be understood that both the foregoing general description and the following detailed description are exemplary, but are not restrictive, of the disclosure.

BRIEF DESCRIPTION OF THE DRAWING

Three further exemplary embodiments of the invention are explained below with reference to thirteen schematic figures but without in any way limiting the invention. In the figures.

DETAILED DESCRIPTION OF THE DISCLOSURE

Figure 1:
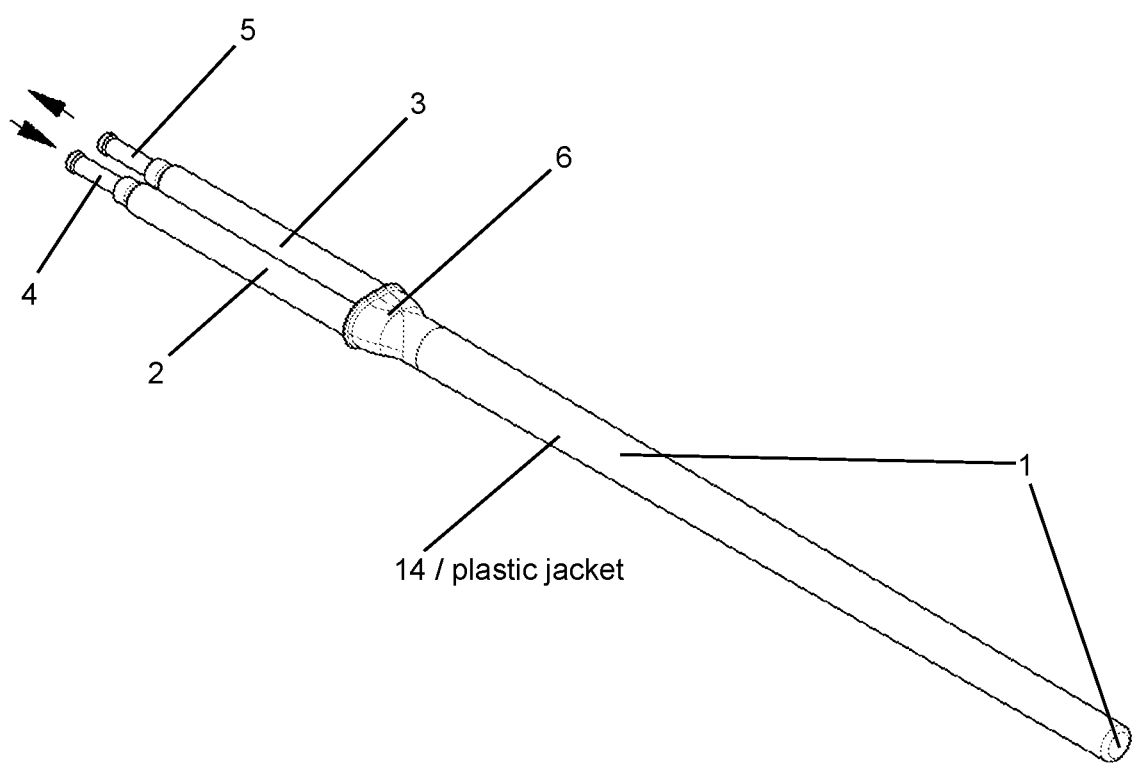
FIG. 1 is a schematic perspective view of a first example of a medical implant according to the invention.

In FIGS. 2 to 4 and 6 to 9 the front end of the respective medical implant is oriented downwards and the rear end upwards. In FIG. 1 the front end of the first example of a medical implant is oriented downwards and to the right and the rear end upwards and to the left. In FIG. 5 the front end of the second example of a medical implant is oriented downwards and to the left and the rear end upwards and to the right.

FIGS. 1 to 4 thus depict the first medical implant according to the invention and FIGS. 5 to 9 depict the second medical implant according to the invention.

The first medical implant according to the invention includes a hollow body 1 of an elastically or plastically deformable plastic material or includes a hollow body 1, the walls of which consist at least in places of a plastic material. The hollow body 1 is a cylindrical tube closed at one end. The hollow body 1 for example consists of a biocompatible plastic material. The hollow body 1 is impermeable to liquids. An inner chamber is arranged inside the hollow body 1.

The material used at least in places for the hollow body 1 is permeable to molecular oxygen and to carbon dioxide. The hollow body 1 or the material from which the hollow body 1 is made to this end has a permeability coefficient for oxygen of greater than or equal to $0.5 \text{ cm}^3/(\text{m}^2*\text{d}*\text{bar})$ and a permeability coefficient for carbon dioxide of greater than or equal to $0.5 \text{ cm}^3/(\text{m}^2*\text{d}*\text{bar})$. The permeability coefficient is determined pursuant to DIN 53380-4 (11/2006).

To feed in a fluid, an inner chamber of the hollow body 1 is connected with a fluid feed line 2 of plastic material. For discharge of the fluid from the hollow body 1, the inner chamber of the hollow body 1 is connected with a fluid discharge line 3 of plastic material. The fluid feed line 2 and the fluid discharge line 3 are flexible and movable at least in places. The fluid feed line 2 has at its rear end (top left in FIG. 1, top in FIGS. 2 to 4) a connector 4, with which the fluid feed line 2 is connected to a fluid source (not shown). The fluid discharge line 3 likewise has a connector 5 at its rear end, with which the fluid discharge line 3 is connected to a receptacle or to an outlet for used fluid.

The fluid feed line 2 and the fluid discharge line 3 are brought together in a connection 6 in which the fluid feed line 2 is guided coaxially into the fluid discharge line 3 or into the hollow body 1. The fluid feed line 2 is arranged coaxially in the hollow body 1. The fluid feed line 2 is guided in the hollow body 1 almost up to the front closed end of the hollow body 1 and there lead through an inflow opening 8 into the hollow body 1. The fluid feed line 2 leads via the inflow opening 8 into the front part of the inner chamber of the hollow body 1. The fluid discharge line 3 is connected via an outflow opening 9 at the opposite rear end of the inner chamber of the hollow body 1 with the inner chamber of the hollow body 1. In this way, it is ensured that the fluid can flow along the surface of the wall of the entire hollow body 1 and gas exchange of oxygen and carbon dioxide can thereby take place through the wall over the entire length of the hollow body 1. The outflow opening 9 is delimited by the connection 6.

A valve 10 in the form of a lip valve is arranged in the fluid feed line 2, the valve 10 allowing flow of the fluid towards the hollow body 1 but preventing flow of the fluid away from the hollow body 1. The valve 10 then acts as a one-way valve. A valve 11 in the form of a lip valve is arranged in the fluid discharge line 3, the valve 11 preventing flow of the fluid toward the hollow body 1 but allowing flow of the fluid away from the hollow body 1. The valve 11 then acts as a one-way valve. The valve 11 in the fluid discharge line 3 is configured to open from a minimum pressure of the fluid. The minimum pressure is preferably adjustable at the valve 11 in the fluid discharge line 3. The minimum pressure may in this respect be selected such that the pressure of the fluid is sufficient to bring the hollow body 1 into a desired outer shape.

The valves 10, 11 are connected with the fluid feed line 2 and the fluid discharge line 3 via valve housings 12, 13. To this end, the fluid feed line 2 slips onto the valve housing 12 and optionally additionally fastened. The fluid discharge line 3 is likewise slipped onto the valve housing 13 and optionally additionally fastened there.

At its rear end, the connector 4 takes the form of a Luer Lock adapter. Likewise, at its rear end the connector 5 takes the form of a Luer Lock adapter. The fluid is fed in and discharged through the connectors 4, 5. The connectors 4, 5 are screwed into the valve housings 12, 13.

The valve housing 12 is of two-part construction to fix the valve 10 in place. The valve housing 12 is connected via an inner thread with an outer thread of the connector 4. The valve housing 13 is of two-part construction to fix the valve 11 in place. The valve housing 13 is connected via an inner thread with an outer thread of the connector 5. All the connections are gas-tight and pressure-tight.

The fluid feed line 2 slips onto the valve housing 12. The fluid feed line 2 is fastened there in a pressure- and gas-tight manner using a crimping sleeve (not shown). The fluid discharge line 3 slips onto the valve housing 13. The fluid discharge line 3 is fastened there in a pressure- and gas-tight manner using a crimping sleeve (not shown).

The hollow body 1 is introduced into a cavity. The hollow body 1, or the medical implant, in this way mechanically supports and stabilizes the cavity. If the medical implant is no longer needed, the hollow body 1 may be compressed by the application of a reduced pressure, it being evacuated for example. The hollow body 1 may then be easily removed from the cavity. If, in particular, the cavity is a cavity in a bone, this bone defect may in this way be carefully treated. Alternatively, the hollow body 1 may also be broken down within the body if it is made of a biodegradable material.

Figure 2:
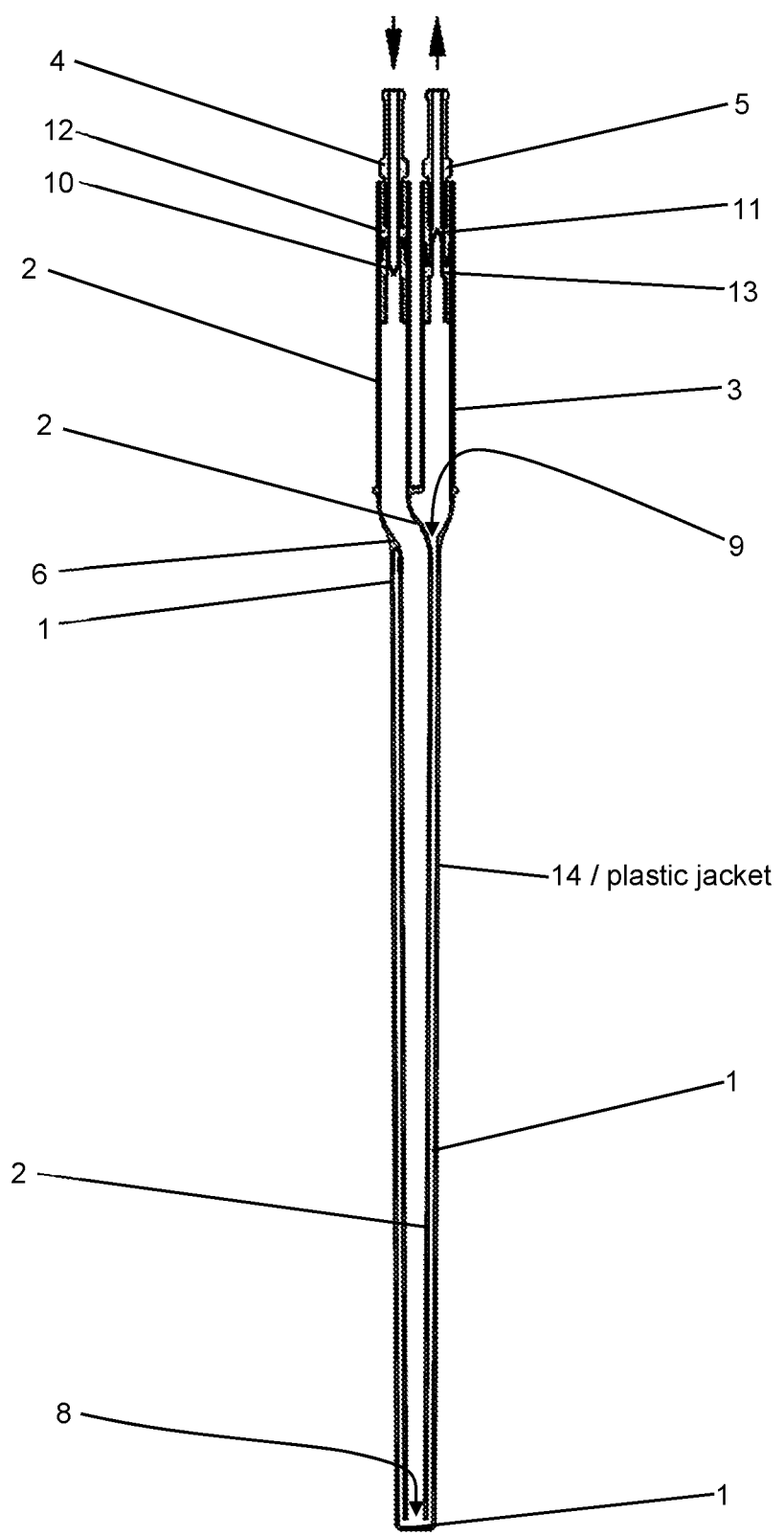
FIG. 2 is a schematic cross-sectional view of the first example of a medical implant according to FIG. 1.
Figure 3:
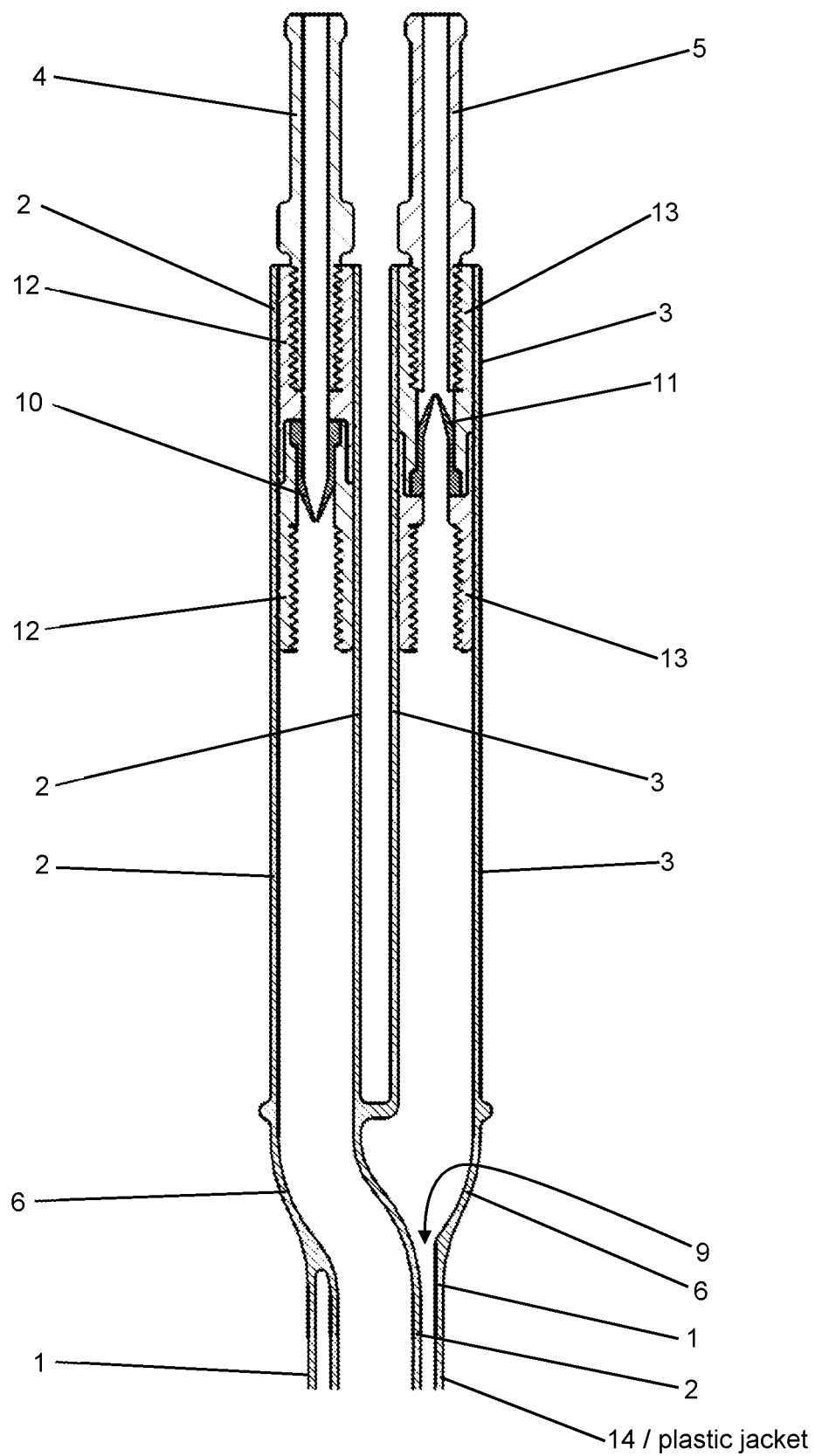
FIG. 3 shows an enlarged detail of the cross-sectional view according to FIG. 2, which shows the rear connectors.
Figure 4:
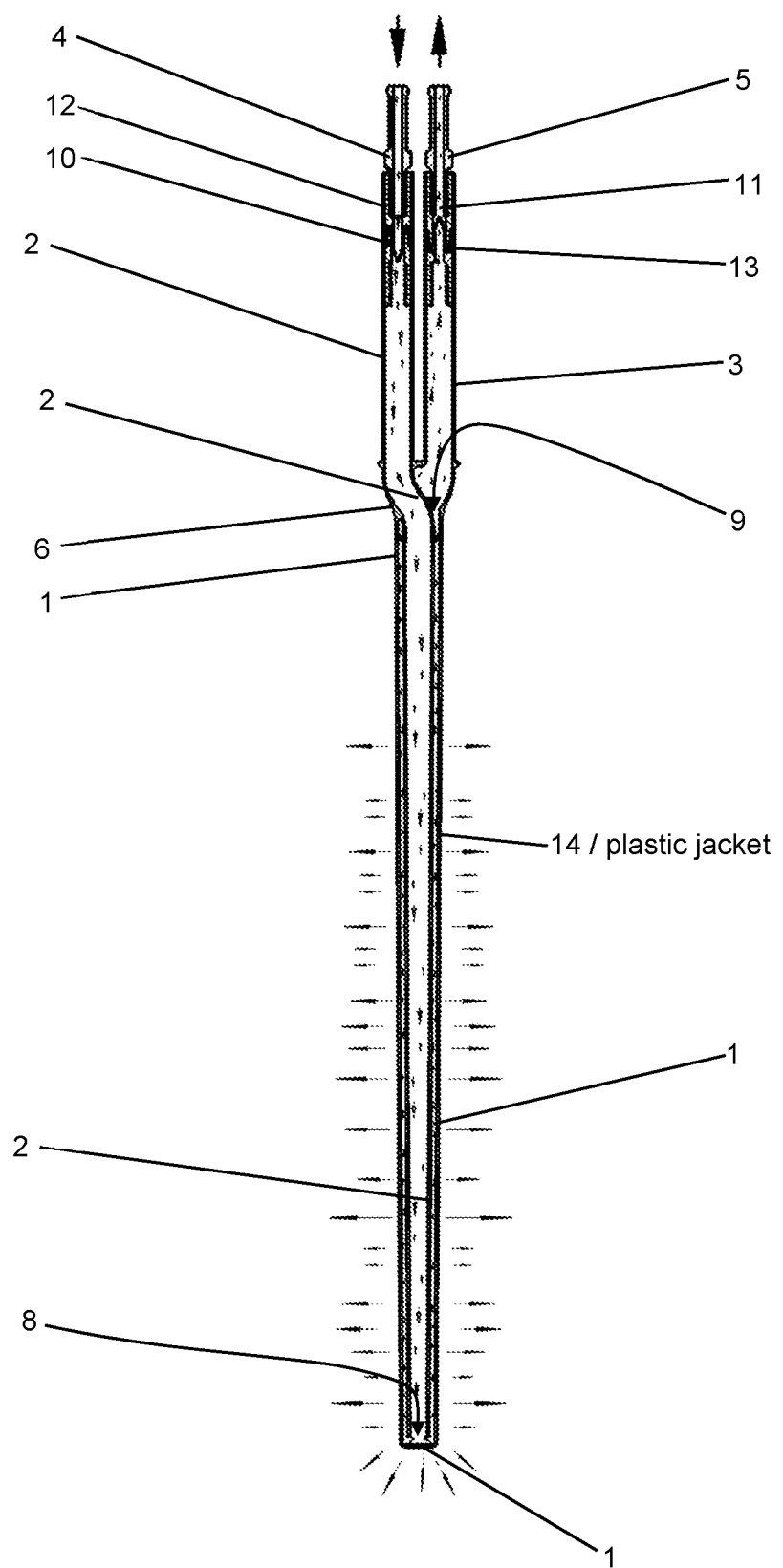
FIG. 4 is a schematic cross-sectional view of the first medical implant according to FIGS. 1 to 3 in which the flow conditions and delivery of oxygen are indicated by pointed arrows.
Figure 5:
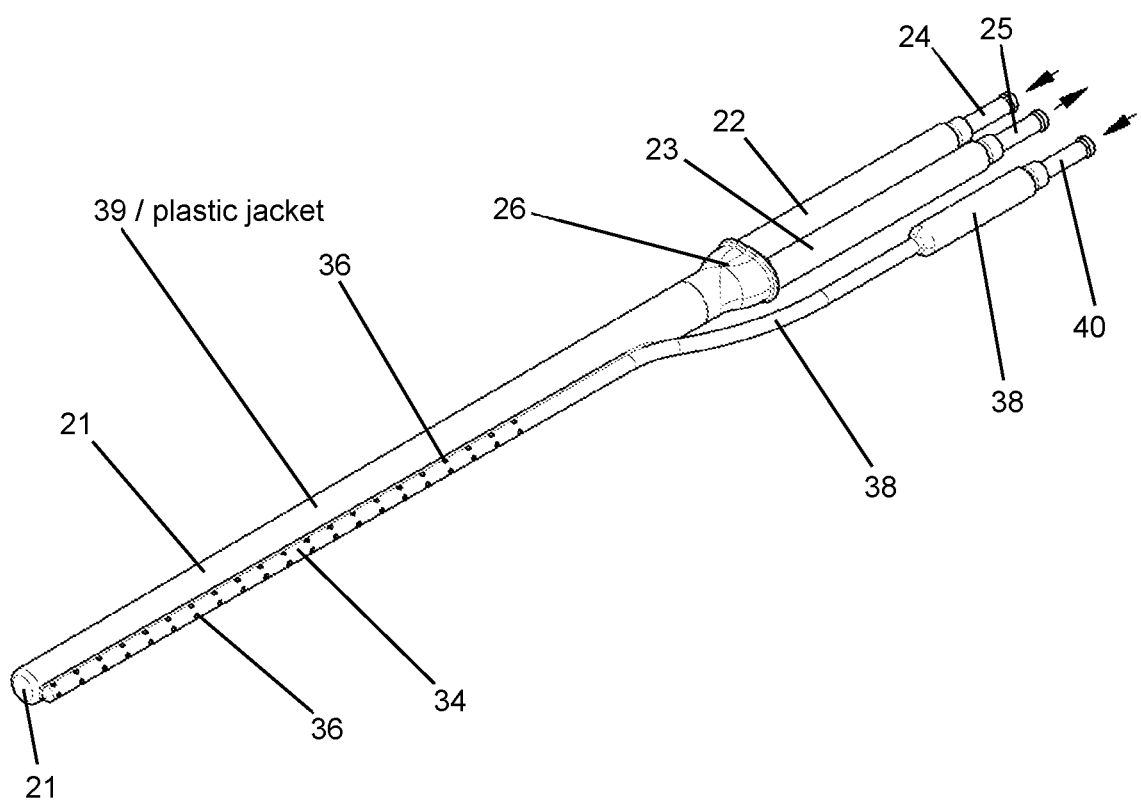
FIG. 5 is a schematic perspective view of a second example of a medical implant according to the invention.
Figure 6:
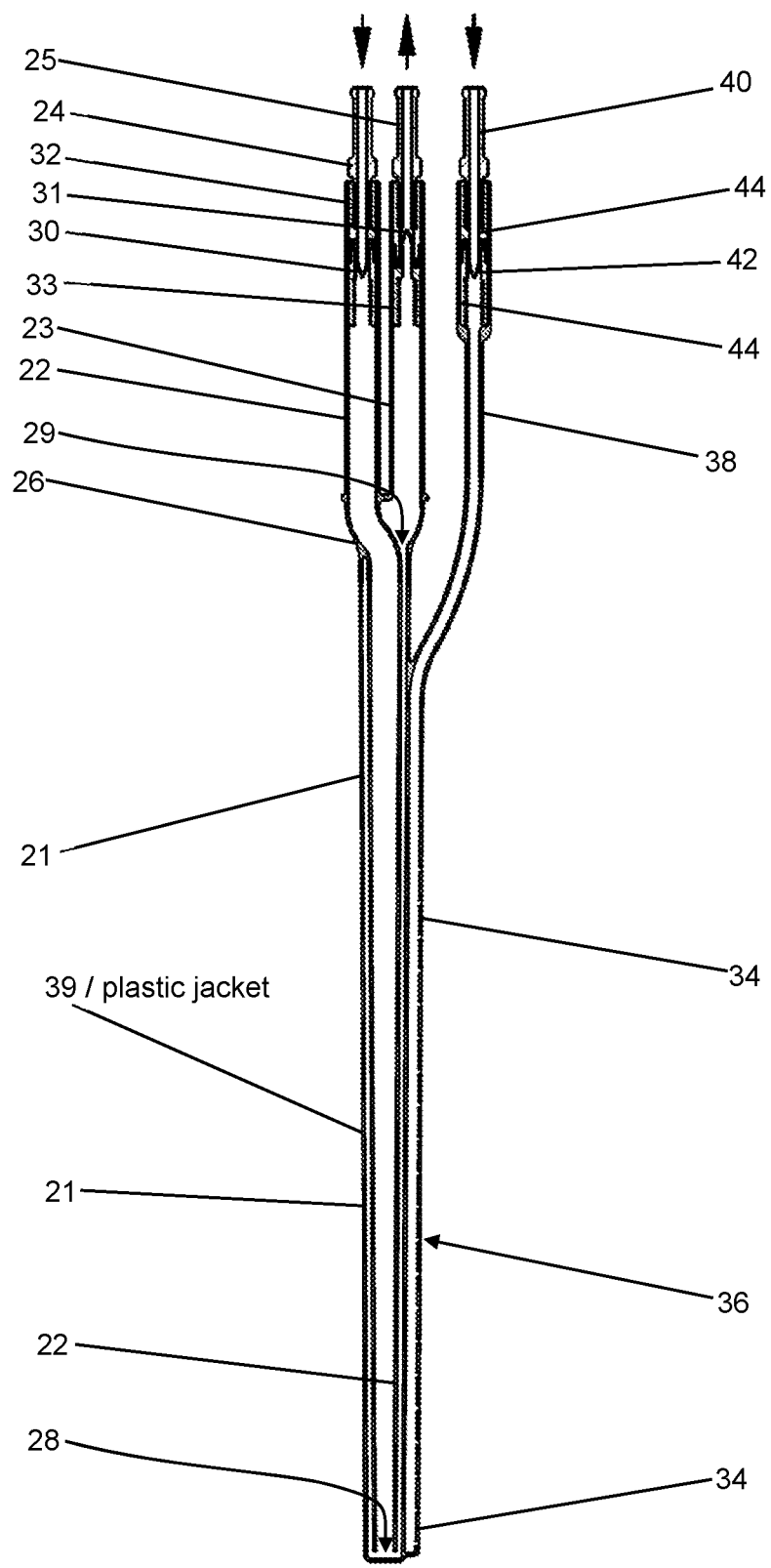
FIG. 6 is a schematic cross-sectional view of the second example of a medical implant according to FIG. 5.

In operation, the fluid is fed through the connector 4 into the medical implant (as indicated in FIGS. 1, 2 and 4 by the pointed arrow pointing into the connector 4). The fluid flows through the fluid feed line 2 and opens the valve 10 when pressure is sufficient. The fluid then flows through the inflow opening 8 into the hollow body 1 and through the hollow body 1. The fluid flows through the fluid discharge line 3 to the initially closed valve 11. In this case, a pressure builds up in the interior of the hollow body 1. As soon as the pressure at the valve 11 in the fluid discharge line 3 is sufficient, the valve 11 opens and the fluid flows out through the fluid discharge line 3 and the connector 5 (as is indicated in FIGS. 1, 2 and 4 by the pointed arrow pointing away from the connector 5).

Oxygen is contained in the fluid. The fluid discharges oxygen through the wall of the hollow body 1 to the surroundings of the hollow body 1. At the same time, the flowing fluid absorbs carbon dioxide, which diffuses through the wall of the hollow body 1 into the inner chamber, from the surroundings of the hollow body 1, and conveys the carbon dioxide away from the medical implant through the connector 5. In this way, the surroundings of the hollow body 1 are supplied with oxygen and the absorption of carbon dioxide prevents over-acidification of the surroundings of the hollow body 1.

Sterile filters (not shown) which are impermeable to microbes but permeable to the fluid may be arranged in the fluid feed line 2 and/or in the fluid discharge line 3. If in particular the fluid is gaseous, this measure can be used without difficulty. If the fluid is liquid, care must be taken to ensure that the sterile filters do not excessively inhibit flow of the fluid. Microbes which might otherwise reach the hollow body 1 and/or might be conveyed away from the hollow body 1 by the connector 5 may be removed from the fluid with the sterile filter. This reduces the risk of infection for the treated patient and the attending personnel. The sterile filter may preferably be arranged in the fluid feed line 2 or the fluid discharge line 3 downstream of the valve 10 or the valve 11 in the direction of flow or the sterile filters may be arranged in the fluid feed line 2 and in the fluid discharge line 3 downstream of the valves 10, 11. Other methods of and options for sterilizing the fluid are also possible. The fluid may for example be sterilized using radiation.

The hollow body 1 and the adjoining regions of the fluid feed line 2 and the fluid discharge line 3 are coated with an antiseptic substance or a soluble antiseptic substance is contained in the material of the hollow body 1, in order to prevent an infection.

The pointed arrows in FIG. 4 in the interior of the hollow body 1, of the fluid feed line 2 and of the fluid discharge line 3 indicate the flow direction of the fluid during operation. Furthermore, the pointed arrows in the region around the hollow body 1 indicate the delivery of oxygen from the fluid.

FIGS. 6 to 9 depict a second embodiment or example of the medical implant according to the invention.

The second medical implant according to the invention includes a hollow body 21 of an elastically or plastically deformable plastic material or includes a hollow body 21, the walls of which consist at least in places of a plastic material. The hollow body 21 is a cylindrical tube closed at one end. The hollow body 21 for example consists of a biocompatible plastic material. The hollow body 21 is impermeable to liquids. An inner chamber is arranged inside the hollow body 21.

The material used at least in places for the hollow body 21 is permeable to molecular oxygen and to carbon dioxide. The hollow body 21 or the material from which the hollow body 21 is made to this end has a permeability coefficient for oxygen of greater than or equal to 0.5 $cm^3/(m^2 \cdot d \cdot bar)$ and a permeability coefficient for carbon dioxide of greater than or equal to 0.5 $cm^3/(m^2 \cdot d \cdot bar)$. The permeability coefficient is determined pursuant to DIN 53380-4 (11/2006).

To feed in a fluid, an inner chamber of the hollow body 21 is connected with a fluid feed line 22 of plastic material. For discharge of the fluid from the hollow body 21, the inner chamber of the hollow body 21 is connected with a fluid discharge line 23 of plastic material. The fluid feed line 22 and the fluid discharge line 23 are flexible and movable at least in places. The fluid feed line 22 has at its rear end (top right in FIG. 5, top in FIGS. 6, 7 and 9) a connector 24, with which the fluid feed line 22 is connected to a fluid source (not shown). The fluid discharge line 23 likewise has a connector 25 at its rear end, with which the fluid discharge line 23 is connected to a receptacle or to an outlet for used fluid.

The fluid feed line 22 and the fluid discharge line 23 are brought together in a connection 26 in which the fluid feed line 22 is guided coaxially into the fluid discharge line 23 or into the hollow body 21. The fluid feed line 22 is arranged coaxially in the hollow body 21. The fluid feed line 22 is guided in the hollow body 21 almost up to the front closed end of the hollow body 21 and there lead through an inflow opening 28 into the hollow body 21. The fluid feed line 22 leads via the inflow opening 28 into the front part of the inner chamber of the hollow body 21. The fluid discharge line 23 is connected via an outflow opening 29 at the opposite rear end of the inner chamber of the hollow body 21 with the inner chamber of the hollow body 21. In this way, it is ensured that the fluid can flow along the surface of the wall of the entire hollow body 21 and gas exchange of oxygen and carbon dioxide can thereby take place through the wall over the entire length of the hollow body 21. The outflow opening 29 is delimited by the connection 26.

A valve 30 in the form of a lip valve is arranged in the fluid feed line 22, the valve 30 allowing flow of the fluid toward the hollow body 21 but preventing flow of the fluid away from the hollow body 21. The valve 30 then acts as a one-way valve. A valve 31 in the form of a lip valve is arranged in the fluid discharge line 23, the valve 31 preventing flow of the fluid toward the hollow body 21 but allowing flow of the fluid away from the hollow body 21. The valve 31 then acts as a one-way valve. The valve 31 in the fluid discharge line 23 is configured to open from a minimum pressure of the fluid. The minimum pressure is preferably adjustable at the valve 31 in the fluid discharge line 23. The minimum pressure may in this respect be selected such that the pressure of the fluid is sufficient to bring the hollow body 21 into a desired outer shape.

The valves 30, 31 are connected with the fluid feed line 22 and the fluid discharge line 23 via valve housings 32, 33. To this end, the fluid feed line 22 slips onto the valve housing 32 and optionally additionally fastened. The fluid discharge line 23 is likewise slipped onto the valve housing 33 and optionally additionally fastened there.

At its rear end, the connector 24 takes the form of a Luer Lock adapter. Likewise, at its rear end the connector 25 takes the form of a Luer Lock adapter. The fluid is fed in and discharged through the connectors 24, 25. The connectors 24, 25 are screwed into the valve housings 32, 33.

The valve housing 32 is of two-part construction to fix the valve 30 in place. The valve housing 32 is connected via an inner thread with an outer thread of the connector 24. The valve housing 33 is of two-part construction to fix the valve 31 in place. The valve housing 33 is connected via an inner thread with an outer thread of the connector 25. All the connections are gas-tight and pressure-tight.

The fluid feed line 22 slips onto the valve housing 32. The fluid feed line 22 is fastened there in a pressure- and gas-tight manner using a crimping sleeve (not shown). The fluid discharge line 23 slips onto the valve housing 33. The fluid discharge line 23 is fastened there in a pressure- and gas-tight manner using a crimping sleeve (not shown).

The hollow body 21 is introduced into a cavity. The hollow body 21, or the medical implant, in this way mechanically supports and stabilizes the cavity. If the implant is no longer needed, the hollow body 21 may be compressed by the application of a reduced pressure, it being evacuated for example. The hollow body 21 may then be removed from the cavity. If, in particular, the cavity is a cavity in a bone, this bone defect may in this way be carefully treated. Alternatively, the hollow body 21 may also be broken down within the body if it is made of a biodegradable material.

In operation, the fluid is fed through the connector 24 into the medical implant (as indicated in FIGS. 5, 6, 7 and 9 by the pointed arrow pointing into the connector 24). The fluid flows through the fluid feed line 22 and opens the valve 30 when pressure is sufficient. The fluid then flows through the inflow opening 28 into the hollow body 21 and through the hollow body 21. The fluid flows through the fluid discharge line 23 to the initially closed valve 31. In this case, a pressure builds up in the interior of the hollow body 21. As soon as the pressure at the valve 31 in the fluid discharge line 23 is sufficient, the valve 31 opens and the fluid flows out through the fluid discharge line 23 and the connector 25 (as is indicated in FIGS. 5, 6, 7 and 9 by the pointed arrow pointing away from the connector 25).

Oxygen is contained in the fluid. The fluid discharges oxygen through the wall of the hollow body 21 to the surroundings of the hollow body 21. At the same time, the flowing fluid absorbs carbon dioxide, which diffuses through the wall of the hollow body 21 into the inner chamber, from the surroundings of the hollow body 21, and conveys the carbon dioxide away from the medical implant through the connector 25. In this way, the surroundings of the hollow body 21 are supplied with oxygen and the absorption of carbon dioxide prevents over-acidification of the surroundings of the hollow body 21.

Sterile filters (not shown) which are impermeable to microbes but permeable to the fluid may be arranged in the fluid feed line 22 and/or in the fluid discharge line 23. If in particular the fluid is gaseous, this measure can be used without difficulty. If the fluid is liquid, care must be taken to ensure that the sterile filters do not excessively inhibit flow of the fluid. Microbes which might otherwise reach the hollow body 21 and/or might be conveyed away from the hollow body 21 by the connector 25 may be removed from the fluid with the sterile filter. This reduces the risk of infection for the treated patient and the attending personnel. The sterile filter may preferably be arranged in the fluid feed line 22 or the fluid discharge line 23 downstream of the valve 30 or the valve 31 in the direction of flow or the sterile filters may be arranged in the fluid feed line 22 and in the fluid discharge line 23 downstream of the valves 30, 31. Other methods of and options for sterilizing the fluid are also possible. The fluid may for example be sterilized using radiation.

The hollow body 21 and the adjoining regions of the fluid feed line 22 and the fluid discharge line 23 are coated with an antiseptic substance or a soluble antiseptic substance is contained in the material of the hollow body 21, in order to prevent an infection.

To treat the surroundings of the hollow body 21, a line 34 with a plurality of through-openings 36 is fastened to the outside of the hollow body 21. The line 34 is connected with an active ingredient feed line 38 impermeable to liquids. The line 34 and the active ingredient feed line 38 are provided for feeding liquids into the openings 36. The active ingredient feed line 38 is connected via a connector 40 with a source of pharmaceutical active ingredient solution. In this way a pharmaceutical active ingredient solution can be delivered at the surface of the line 34 or of the hollow body 21.

To prevent backflow of liquids from the line 34, a valve 42 is arranged between the active ingredient feed line 38 and the connector 40. The valve 42 is preferably a one-way valve, such as for example a lip valve. The valve 42 is connected with the active ingredient feed line 38 via a valve housing 44. To this end, the active ingredient feed line 38 slips onto the valve housing 44 and optionally additionally fastened. At its rear end, the connector 40 takes the form of a Luer Lock adapter. The valve housing 44 is of two-part construction to fix the valve 42 in place. The valve housing 44 is connected via an inner thread with an outer thread of the connector 40. The active ingredient feed line 38 slips onto the valve housing 44.

Figure 7:
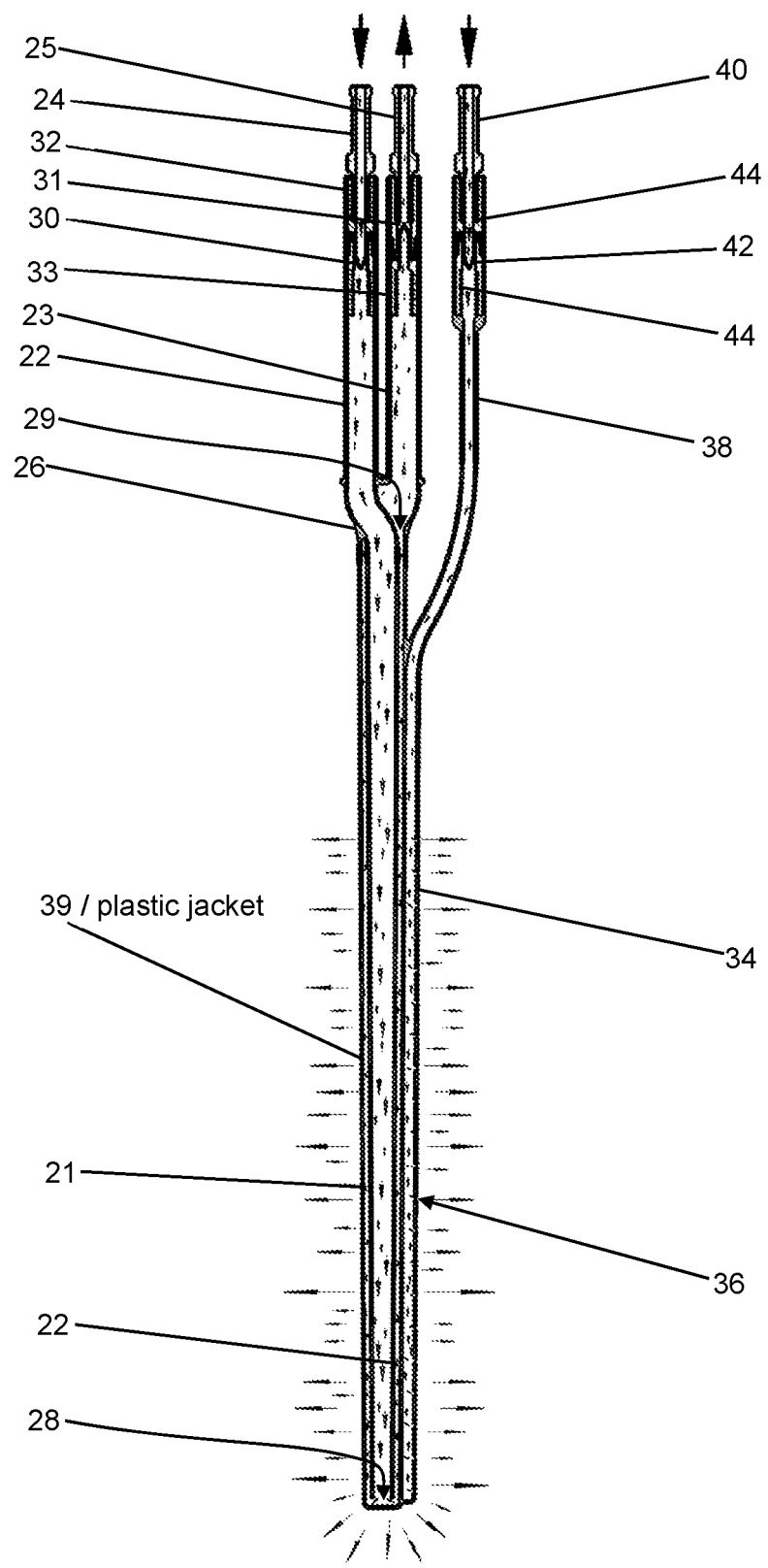
FIG. 7 is a schematic cross-sectional view of the second medical implant according to FIGS. 5 and 6, wherein the flow conditions and delivery of oxygen are indicated by pointed arrows.
Figure 8:
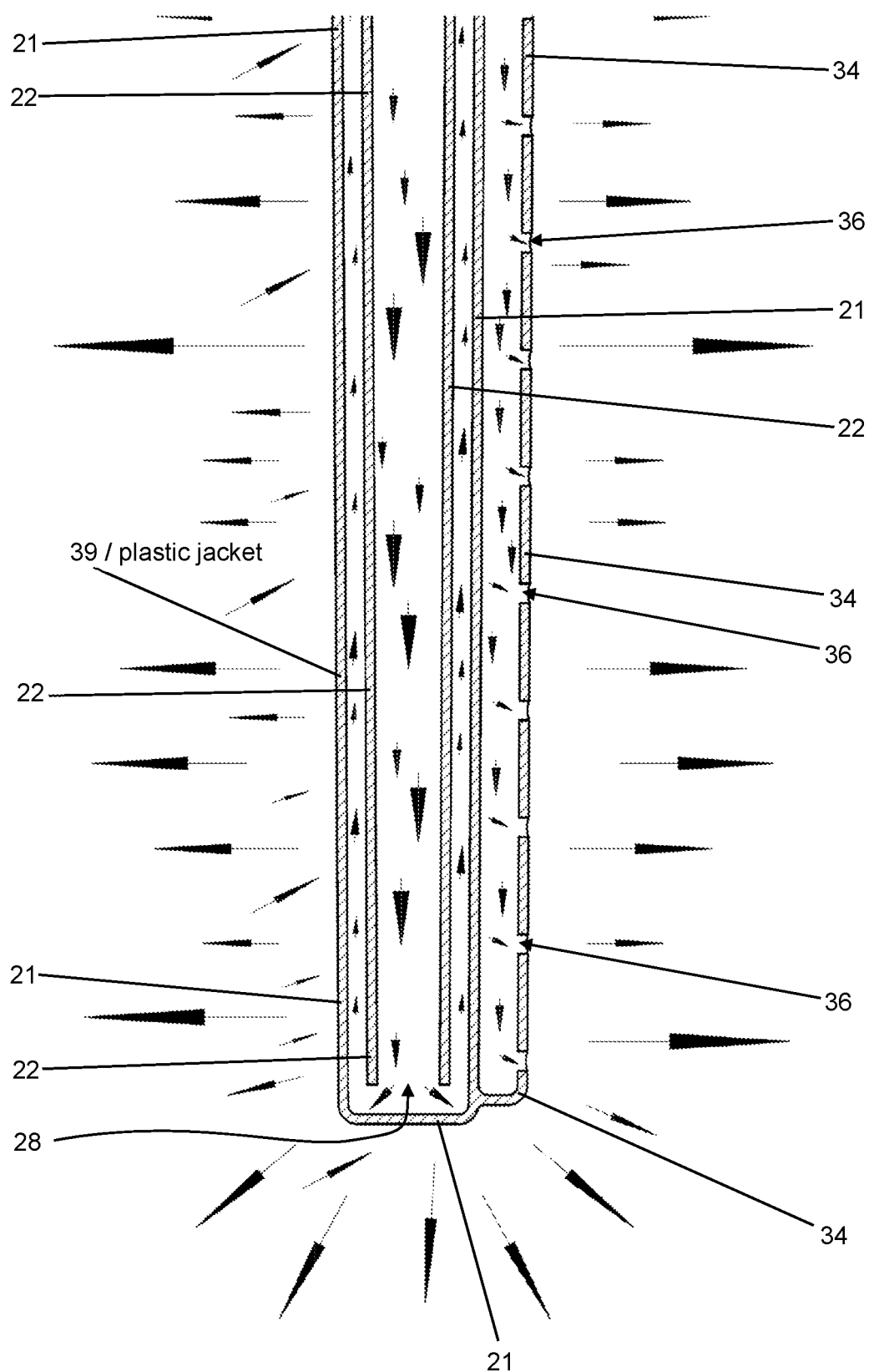
FIG. 8 shows an enlarged detail of the cross-sectional views according to FIGS. 6 and 7, which shows the front end of the medical implant, wherein the flow conditions and the delivery of oxygen and the absorption of carbon dioxide are indicated by pointed arrows.
Figure 9:
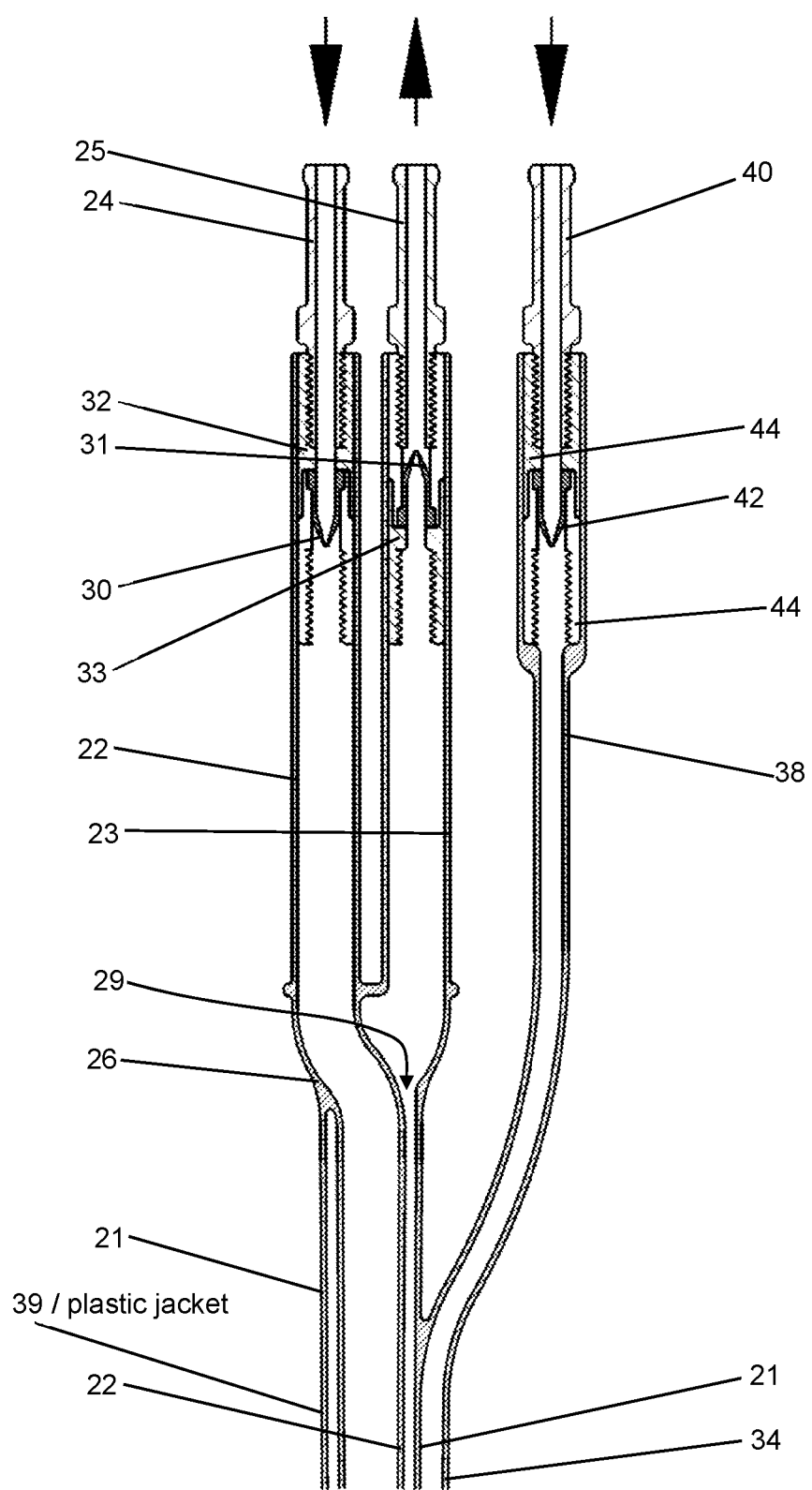
FIG. 9 shows an enlarged detail of the cross-sectional views according to FIGS. 6 and 7, showing the rear connectors.
Figure 10:
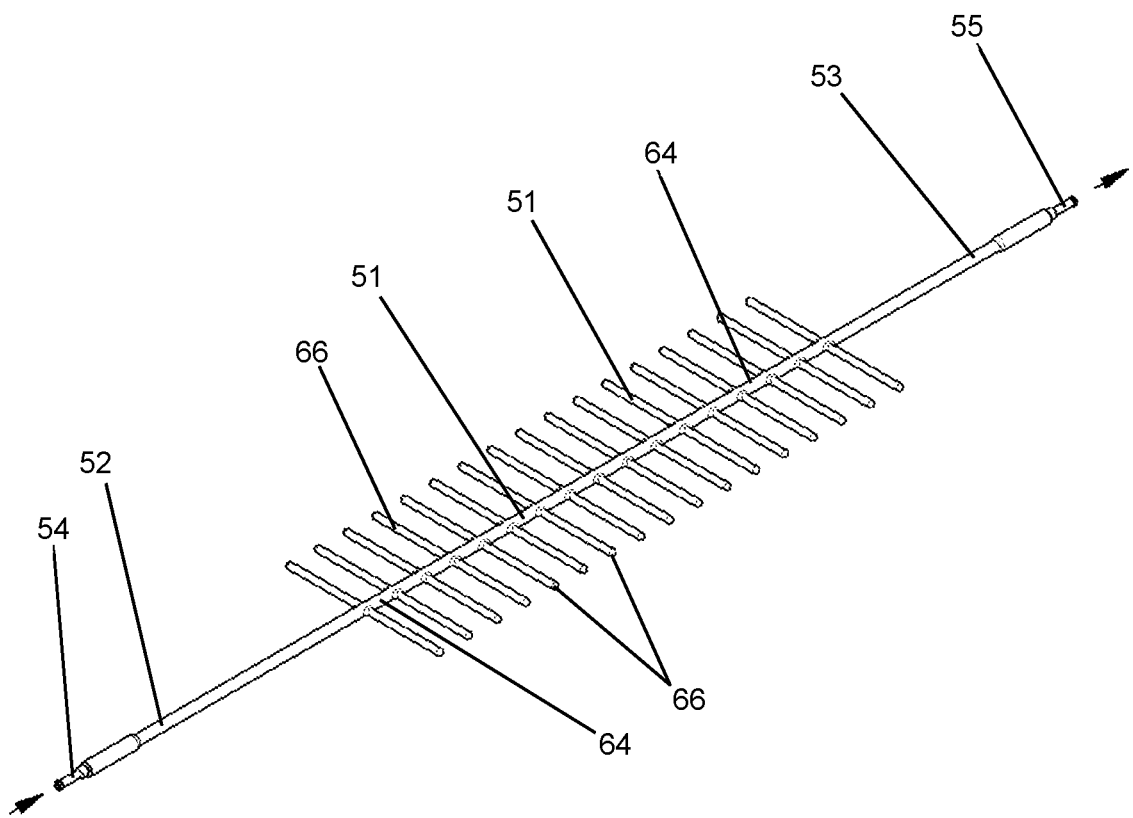
FIG. 10 is a schematic perspective view of a third example of a medical implant according to the invention.

The pointed arrows in FIGS. 7 and 8 in the interior of the hollow body 21, of the fluid feed line 22 and of the fluid discharge line 23 indicate the flow direction of the fluid during operation. The pointed arrows in line 34 likewise indicate the flow and delivery of a liquid medical active ingredient. Furthermore, the pointed arrows in the region around the hollow body 21 indicate the delivery of oxygen from the fluid (FIGS. 7 and 8) and a number of smaller pointed arrows indicate the absorption of carbon dioxide (only in FIG. 8).

FIGS. 10 to 13 depict a third exemplary embodiment of a medical implant according to the invention.

The third medical implant according to the invention has a hollow body 51 of a plastically deformable plastic material with incorporated metal wires or an incorporated metal matrix. The hollow body 51 has a main part 64 and a plurality of branches 66 respectively opposite one another in pairs and extending perpendicularly away from the main part 64. The lateral branches 66 may project approximately 2 mm from the main part 64.

The hollow body 51 for example consists of a biocompatible plastic material. The hollow body 51 is impermeable to liquids. In the interior of the hollow body 51 and thus also in the interior of the main part 64 and of the branches 66, an inner chamber is arranged in the hollow body 51.

The material used at least in places for the hollow body 51 is permeable to molecular oxygen and to carbon dioxide. The hollow body 51 or the material from which the hollow body 51 is made to this end has a permeability coefficient for oxygen of greater than or equal to 0.5 $cm^3/(m^2*d*bar)$ and a permeability coefficient for carbon dioxide of greater than or equal to 0.5 $cm^3/(m^2*d*bar)$. The permeability coefficient is determined pursuant to DIN 53380-4 (11/2006).

To feed in a fluid, an inner chamber of the hollow body 51 is connected with a fluid feed line 52 of plastic material. For discharge of the fluid from the hollow body 51, the inner chamber of the hollow body 51 is connected with a fluid discharge line 53 of plastic material. The fluid feed line 52 and the fluid discharge line 53 are flexible and movable at least in places. The fluid feed line 52 has a connector 54 with which the fluid feed line 52 is connected to a fluid source (not shown). The fluid discharge line 53 likewise has a connector 55, with which the fluid discharge line 53 is connected to a receptacle or to an outlet for used fluid.

The fluid feed line 52 and the fluid discharge line 53 open into the hollow body 51 or the main part 64 on opposing sides of the hollow body 51. The fluid feed line 52 leads via the inflow opening 58 into the inner chamber of the hollow body 51. The fluid discharge line 53 is connected via an outflow opening 59 at the opposite end of the inner chamber of the hollow body 51 with the inner chamber of the hollow body 51. In this way, it is ensured that the fluid can flow along the surface of the wall of the entire hollow body 51 and gas exchange of oxygen and carbon dioxide can thereby take place through the wall over the entire length of the hollow body 51 and also in the branches 66 thereof.

A valve 60 in the form of a lip valve is arranged in the fluid feed line 52, the valve 60 allowing flow of the fluid toward the hollow body 51 but preventing flow of the fluid away from the hollow body 51. The valve 60 then acts as a one-way valve. A valve 61 in the form of a lip valve is arranged in the fluid discharge line 53, the valve 61 preventing flow of the fluid toward the hollow body 51 but allowing flow of the fluid away from the hollow body 51. The valve 61 then acts as a one-way valve. The valve 61 in the fluid discharge line 53 is configured to open from a minimum pressure of the fluid. The minimum pressure is preferably adjustable at the valve 61 in the fluid discharge line 53. The minimum pressure may in this respect be adjusted such that the pressure of the fluid is sufficient to bring the hollow body 51 into a desired outer shape.

The valves 60, 61 are connected with the fluid feed line 52 and the fluid discharge line 53 via valve housings 62, 63. To this end, the fluid feed line 52 slips onto the valve housing 62 and optionally additionally fastened. The fluid discharge line 53 is likewise slipped onto the valve housing 63 and optionally additionally fastened there.

At its rear end, the connector 54 takes the form of a Luer Lock adapter. Likewise, at its rear end the connector 55 takes the form of a Luer Lock adapter. The fluid is fed in and discharged through the connectors 54, 55. The connectors 54, 55 are screwed into the valve housings 62, 63.

The valve housing 62 is of two-part construction to fix the valve 60 in place. The valve housing 62 is connected via an inner thread with an outer thread of the connector 54. The valve housing 63 is of two-part construction to fix the valve 61 in place. The valve housing 63 is connected via an inner thread with an outer thread of the connector 55. All the connections are gas-tight and pressure-tight.

The fluid feed line 52 slips onto the valve housing 62. The fluid feed line 52 is fastened there in a pressure- and gas-tight manner using a crimping sleeve (not shown). The fluid discharge line 53 slips onto the valve housing 13. The fluid discharge line 53 is fastened there in a pressure- and gas-tight manner using a crimping sleeve (not shown).

Figure 11:
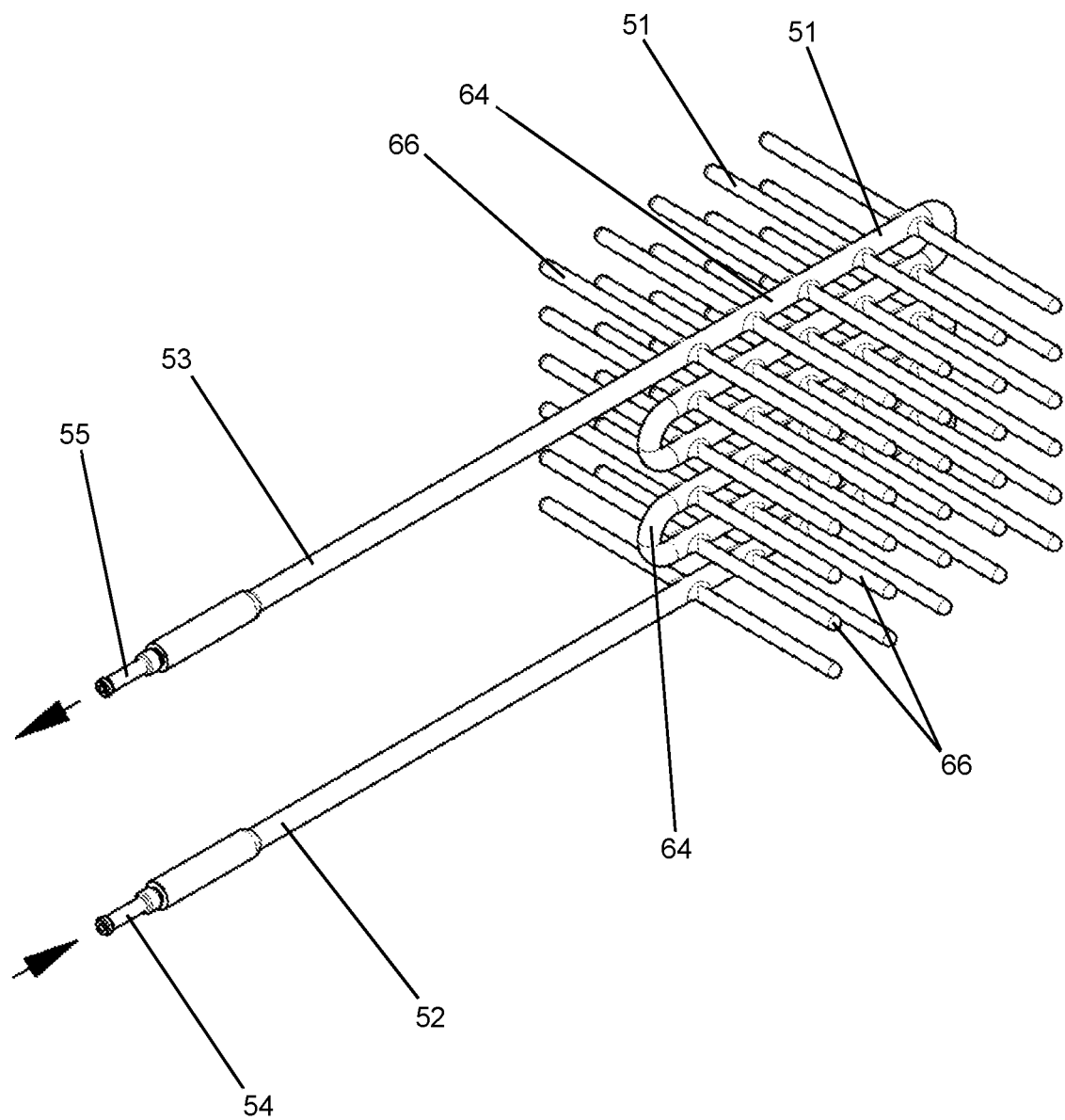
FIG. 11 is a schematic perspective view of the third example of a medical implant in a folded state.

The hollow body 51 may be folded, to produce a three-dimensional structure (see FIG. 11). The hollow body 51 may moreover be used for supply and growth of cell cultures of bone cells, which are arranged on the surface of the hollow body 51. The hollow body 51 prepared in this way is then introduced into a cavity. The hollow body 51, or the medical implant, in this way mechanically supports and stabilizes the cavity. If the medical implant is no longer needed, the hollow body 51 may be compressed by the application of a reduced pressure, it being evacuated for example. The hollow body 51 may then be easily removed from the cavity. If, in particular, the cavity is a cavity in a bone, this bone defect may in this way be carefully treated. Alternatively, the hollow body 51 may also be broken down within the body if it is made of a biodegradable material.

In operation, the fluid is fed through the connector 54 into the medical implant (as indicated in FIGS. 10 to 13 by the pointed arrow pointing into the connector 54). The fluid flows through the fluid feed line 52 and opens the valve 60 when pressure is sufficient. The fluid then flows through the inflow opening 58 into the hollow body 51 and through the main part 64 and the branches 66 of the hollow body 51. The fluid flows through the fluid discharge line 53 to the initially closed valve 61. In this case, a pressure builds up in the interior of the hollow body 51. As soon as the pressure at the valve 61 in the fluid discharge line 53 is sufficient, the valve 61 opens and the fluid flows out through the fluid discharge line 53 and the connector 55 (as is indicated in FIGS. 10 to 13 by the pointed arrow pointing away from the connector 55).

Oxygen is contained in the fluid. The fluid discharges oxygen through the wall of the hollow body 51 to the surroundings of the hollow body 51. At the same time, the flowing fluid absorbs carbon dioxide, which diffuses through the wall of the hollow body 51 into the inner chamber, from the surroundings of the hollow body 51, and conveys the carbon dioxide away from the medical implant through the connector 55. In this way, the surroundings of the hollow body 51 are supplied with oxygen and the absorption of carbon dioxide prevents over-acidification of the surroundings of the hollow body 51.

Sterile filters (not shown) which are impermeable to microbes but permeable to the fluid may be arranged in the fluid feed line 52 and/or in the fluid discharge line 53. If in particular the fluid is gaseous, this measure can be used without difficulty. If the fluid is liquid, care must be taken to ensure that the sterile filters do not excessively inhibit flow of the fluid. Microbes which might otherwise reach the hollow body 51 and/or might be conveyed away from the hollow body 51 by the connector 55 may be removed from the fluid with the sterile filter. This reduces the risk of infection for the treated patient and the attending personnel. The sterile filter may preferably be arranged in the fluid feed line 52 or the fluid discharge line 53 downstream of the valve 60 or the valve 61 in the direction of flow or the sterile filters may be arranged in the fluid feed line 52 and in the fluid discharge line 53 downstream of the valves 60, 61. Other methods of and options for sterilizing the fluid are also possible. The fluid may for example be sterilized using radiation.

The hollow body 51 and optionally the adjoining regions of the fluid feed line 52 and the fluid discharge line 53 are coated with an antiseptic substance or a soluble antiseptic substance is contained in the material of the hollow body 51, in order to prevent an infection.

Figure 12:
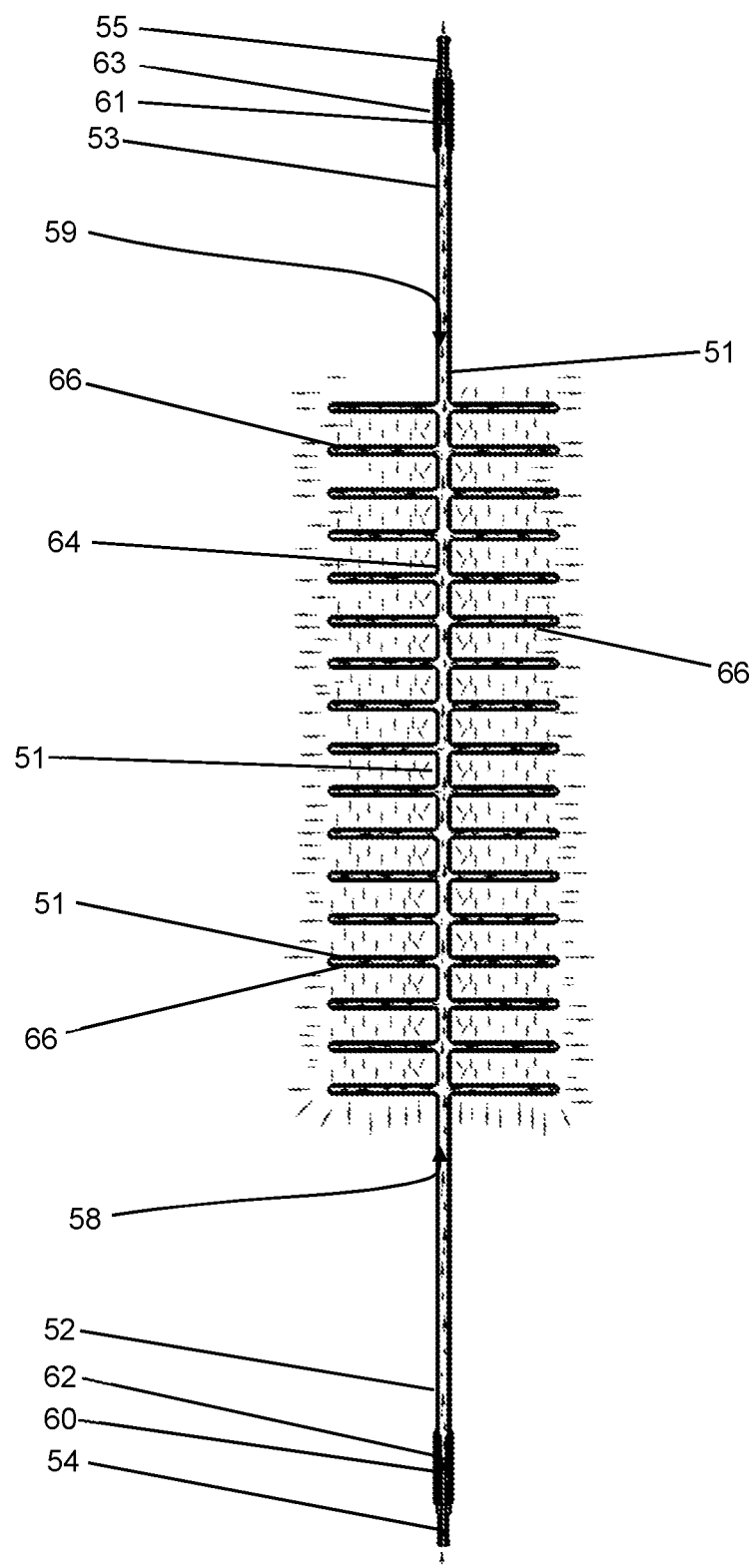
FIG. 12 is a schematic cross-sectional view of the third example of a medical implant according to FIG. 10, wherein the flow conditions and the delivery of oxygen and the absorption of carbon dioxide are indicated by pointed arrows.
Figure 13:
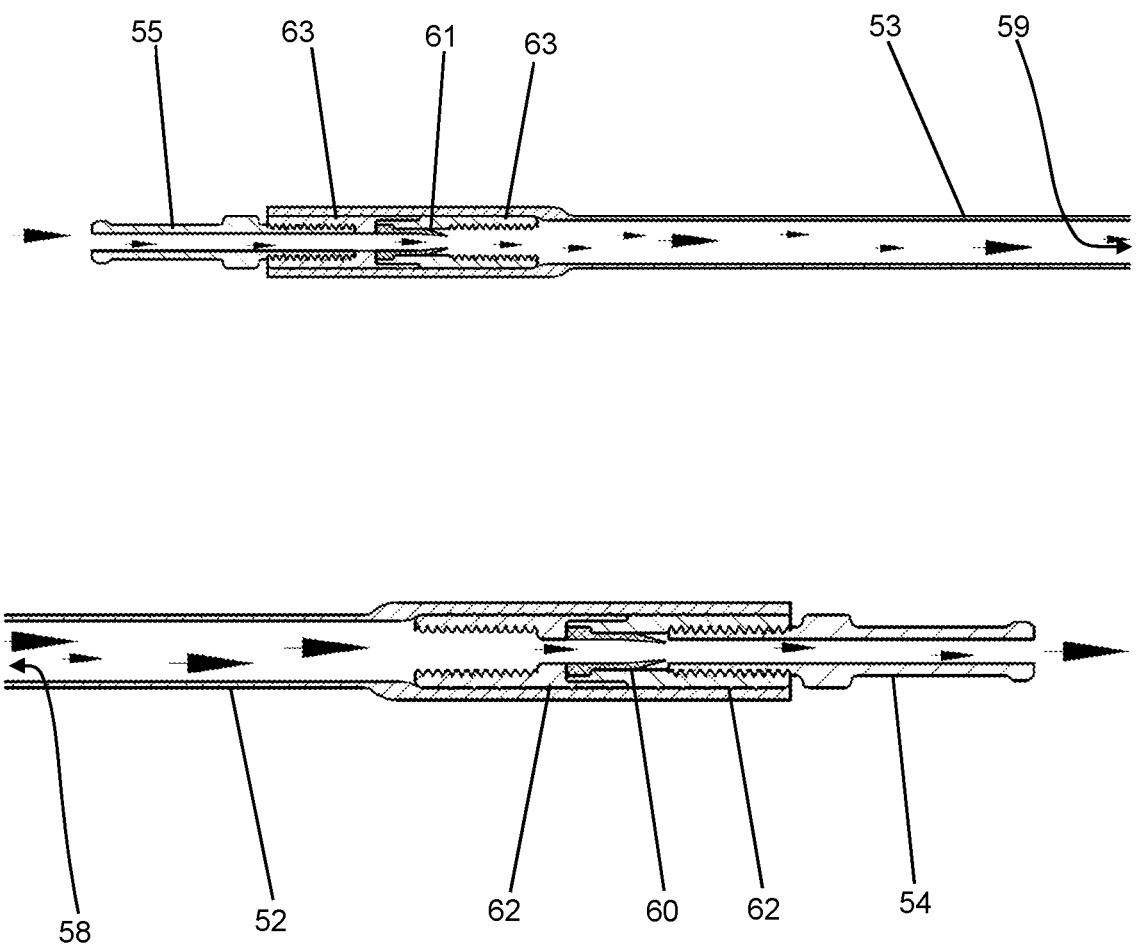
FIG. 13 shows an enlarged detail of the cross-sectional view according to FIG. 12, which shows the connectors.

The pointed arrows in FIG. 12 in the interior of the hollow body 51, of the fluid feed line 52 and of the fluid discharge line 53 indicate the flow direction of the fluid during operation. Furthermore, the pointed arrows in the region around the hollow body 51 indicate the delivery of oxygen from the fluid.

The medical implant may be used extracorporeally to aerate and multiply a cell culture for bone cells at the surface of the hollow body 1, 21, 51. Once provided with the grown cell culture, the medical implant may subsequently be implanted and then aerated still further inside the body, in order to promote further multiplication and growth of the cells in the bone defect.

The features of the invention disclosed in the above description, as well as in the claims, figures, and exemplary embodiments, may be essential both individually and in any desired combination to realization of the invention in its various embodiments. Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure.

AMENDMENTS TO THE SPECIFICATION

The applicant respectfully requests that, before formally examining the application identified above, the Examiner accept the enclosed substitute specification under 37 C.F.R. § 1.125. The applicant believes that the substitute specification will facilitate processing of the application in accordance with M.P.E.P. § 608.01(q) and asserts that it complies with 37 C.F.R. § 1.52. Although it makes no substantive changes, the substitute specification is submitted to conform this case to the formal requirements and long-established formal standards of U.S. Patent and Trademark Office practice, and to provide improved idiom and better grammatical form. Also, enclosed and submitted is a marked-up copy which shows the portions of the original specification which are being added and deleted.

STATEMENT

The undersigned, an attorney registered to practice before the U.S. Patent and Trademark Office, hereby states that the enclosed substitute specification contains no new matter and includes the same changes as are indicated in the marked-up copy of the original specification.

The invention claimed is:

1. A medical implant for treating bone defects using a fluid, the medical implant comprising:
    at least one hollow body which delimits an inner chamber having an inner surface in the interior of the hollow body;
    at least one fluid feed line which is connected in a fluid-permeable manner with the inner chamber of the hollow body and configured to conduct the fluid; and
    at least one fluid discharge line which is connected in a fluid-permeable manner with the inner chamber of the hollow body and configured to conduct the fluid;
    wherein the hollow body consists at least in places of at least one plastic material, wherein the at least one plastic material is impermeable to liquids and is permeable to oxygen and to carbon dioxide, such that oxygen is deliverable from the fluid passed through the hollow body to the surroundings of the hollow body and carbon dioxide is absorbable from the surroundings of the hollow body into the fluid, and wherein the hollow body or the at least one plastic material of the hollow body has a permeability coefficient for oxygen of greater than or equal to $0.5 \text{ cm}^3/(\text{m}^2 \cdot \text{d} \cdot \text{bar})$ and a permeability coefficient for carbon dioxide of greater than or equal to $0.5 \text{ cm}^3/(\text{m}^2 \cdot \text{d} \cdot \text{bar})$.

2. The medical implant according to claim 1, wherein the hollow body or the at least one plastic material of the hollow body has a permeability coefficient for oxygen of greater than or equal to $1.0 \text{ cm}^3/(\text{m}^2 \cdot \text{d} \cdot \text{bar})$ and a permeability coefficient for carbon dioxide of greater than or equal to $1.0 \text{ cm}^3/(\text{m}^2 \cdot \text{d} \cdot \text{bar})$.

3. The medical implant according to claim 1, wherein the fluid feed line and the fluid discharge line lead in such a way into the hollow body that, when the fluid from the fluid feed line flows through the hollow body into the fluid discharge line, the fluid flows over at least over 50% of the entire inner surface of the hollow body.

4. The medical implant according to claim 1, wherein the fluid feed line has an inflow opening that leads the fluid feed line into the inner chamber, the fluid discharge line has an outflow opening that forms a point where the inner chamber opens into the fluid discharge line, and the inflow opening of the fluid feed line is arranged spatially separately from the outflow opening of the fluid discharge line.

5. The medical implant according to claim 4, wherein the hollow body has a first end and an opposite second end and the inflow opening of the fluid feed line is arranged at the first end of the hollow body and the outflow opening of the fluid discharge line is arranged at the second end of the hollow body opposite the first end.

6. The medical implant according to claim 1, wherein the hollow body has a side and the fluid feed line and the fluid discharge line are both jointly connected with the hollow body on the side of the hollow body.

7. The medical implant according to claim 1, further comprising at least one valve arranged in one or both of the fluid feed line and the fluid discharge line.

8. The medical implant according to claim 1, wherein the fluid feed line and the fluid discharge line consist of a material which is not permeable to oxygen and carbon dioxide.

9. The medical implant according to claim 1, wherein the hollow body or the at least one plastic material of the hollow body contains at least one antiseptic active ingredient or is coated with at least one antiseptic active ingredient.

10. The medical implant according to claim 1, wherein at least a portion of the hollow body is a hollow cylinder with opposing base faces and the fluid feed line and the fluid discharge line lead into the hollow cylinder in the region of the opposing base faces of the hollow cylinder, and wherein the hollow cylinder coaxially surrounds at least a part of the fluid feed line or of the fluid discharge line.

11. The medical implant according to claim 1, further comprising a perforated metal body or a plastic material body having an outside covered with a plastic layer permeable to oxygen and to carbon dioxide and in which the hollow body is embedded.

12. The medical implant according to claim 1, wherein the hollow body has a plastically deformable plastic jacket permeable to oxygen and carbon dioxide.

13. The medical implant according to claim 1, further comprising:
    an active ingredient feed line with a free cross-section for delivering an active ingredient; and
    a line with a free cross-section and a plurality of openings having free cross-sectional areas for delivering an active ingredient arranged on the hollow body and connected with the active ingredient feed line,
    wherein the sum of the free cross-sectional areas of the openings is less than the free cross-section of the line and of the active ingredient feed line.

14. The medical implant according to claim 1, wherein the at least one plastic material is an elastic and/or plastic, non-biodegradable plastic material, wherein the at least one plastic material is selected from polyurethane, ethylene-propylene-diene rubber and silicone, or the at least one plastic material is an elastic and/or plastic biodegradable plastic material.

15. The medical implant according to claim 1, wherein the hollow body is configured to expand and/or contract in response to changing pressure in the inner chamber thereof relative to the surrounding atmosphere.

16. The medical implant according to claim 1, wherein the hollow body has a main part and a plurality of branches extending laterally from the main part, wherein the inner chamber of the hollow body extends in the main part and in the branches and the fluid feed line and the fluid discharge line are connected with the main part, and wherein the branches consist of the at least one plastic material.

17. The medical implant according to claim 1, wherein the hollow body consists of at least one absorbable and/or biodegradable material.

18. A bone defect treatment system having a medical implant according to claim 1 and the fluid, wherein the fluid contains oxygen and is suitable for absorbing carbon dioxide.

19. The bone defect treatment system according to claim 18, wherein the fluid is selected from air, oxygen, oxygen-saturated saline, oxygen-saturated Ringer's solution, oxygen-saturated Ringer's lactate solution, oxygen-saturated phosphate buffer solution and oxygen-saturated perfluorodecalin or a mixture of at least two of the stated gases or liquids.

20. The bone defect treatment system according to claim 18, further comprising a bone substitute material, wherein the hollow body has an external surface and the bone substitute material is configured to be applied to the external surface of the hollow body.

21. The bone defect treatment system according to claim 20, wherein the bone substitute material is selected from a non-biodegradable, a partially degradable or a fully biodegradable bone substitute material and mixtures thereof.

22. The bone defect treatment system according to claim 20, wherein the bone substitute material has a surface and is selected from autologous bone tissue, allogeneic bone tissue, hydroxyapatite, carbonate apatite, β-tricalcium phosphate, α-tricalcium phosphate, calcium dihydrate, brushite, monetite and mixtures thereof, or the bone substitute material contains living cells and/or is colonized with living cells on the surface thereof.

23. A method for gas-flushing a surface of a medical implant with a bone defect treatment system, the method comprising the following steps:
A) feeding a fluid containing oxygen into an inner chamber of a hollow body of the medical implant through at least one fluid feed line;
B) delivering oxygen from the fluid through a plastic material delimiting the inner chamber of the hollow body to the surroundings of the hollow body;
C) absorbing gaseous carbon dioxide from the surroundings of the hollow body through the plastic material delimiting the inner chamber into the fluid;
D) passing the fluid through the inner chamber of the hollow body; and
E) discharging the fluid from the inner chamber of the hollow body through at least one fluid discharge line.

24. The method according to claim 23, wherein the method is not performed for medical treatment of a human or animal body.

25. The method according to claim 23, further comprising the steps of introducing the hollow body into a cavity prior to step A) and applying a bone substitute material to the surface of the medical implant and/or introducing the bone substitute material into the cavity between the medical implant and the inner walls delimiting the cavity.

26. The method according to claim 23, further comprising the step of applying bone cells, prior to step A), together with a nutrient solution and/or growth promoting substances, to the external surface of the hollow body.

* * * * *